(12) United States Patent
Pichersky et al.

(10) Patent No.: US 8,124,375 B2
(45) Date of Patent: *Feb. 28, 2012

(54) GERANIOL SYNTHASE, METHODS OF PRODUCTION AND USES THEREOF

(75) Inventors: Eran Pichersky, Chelsea, MI (US); Yoko Iijima, Chiba (JP); Efraim Lewinsohn, Timrat, IL (US); David R. Gang, Tucson, AZ (US); James Simon, Princeton, NJ (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/702,019

(22) Filed: Feb. 8, 2010

(65) Prior Publication Data

US 2010/0209969 A1 Aug. 19, 2010

Related U.S. Application Data

(63) Continuation of application No. 10/582,549, filed as application No. PCT/US2004/040321 on Dec. 2, 2004, now Pat. No. 7,704,716.

(60) Provisional application No. 60/528,202, filed on Dec. 10, 2003.

(51) Int. Cl.
C07H 21/04 (2006.01)
C12N 15/63 (2006.01)
C12N 5/10 (2006.01)

(52) U.S. Cl. ............... 435/69.1; 435/252.33; 435/254.2; 435/320.1; 435/348; 536/23.6

(58) Field of Classification Search ................. None
See application file for complete search history.

(56) References Cited

OTHER PUBLICATIONS

William R. Pearson Empirical Statistical Estimates for Sequence Similarity Searches Journal of Molecular Biology vol. 276, Issue 1, Feb. 13, 1998, pp. 71-84.*
Lucker et al (Monoterpene biosynthesis in lemon (Citus Lemon) cDNA isolation and functional analysis of four monoterpene synthetases Eur. J. of Biochemistry 269, 3160-3171 (2002) FEBS.*

* cited by examiner

*Primary Examiner* — Kagnew H Gebreyesus
(74) *Attorney, Agent, or Firm* — Harness, Dickey & Pierce, P.L.C.

(57) ABSTRACT

The present invention relates to novel type of monoterpene synthase, a key enzyme in the production of the monoterpene aroma compound geraniol. More specifically, the present invention relates to nucleic acid sequences coding for GES from flowers and herbs species, in particular sweet basil, as well as to vectors containing the sequences, to host cells containing the sequences and to methods of producing recombinant GES, its products, and uses thereof.

10 Claims, 8 Drawing Sheets

```
atgtcttgtg cacggatcac cgtaacattg ccgtatcgct ccgcaaaaac
atcaattcaa cggggaatta cgcattaccc cgcccttata cgcccacgct
tctctgcttg cacgcctttg gcatcggcga tgcctctaag ttcaactcct
ctcatcaacg gggataactc tcagcgtaaa aacacacgtc aacacatgga
ggagagcagc agcaagagga gagaatatct gctggaggaa acgacgcgaa
aactgcagag aaacgacacc gaatcggtgg agaaactcaa gcttatcgac
aacatccaac agttgggaat cggctactat tttgaggacg ccatcaacgc
cgtactccgc tcgcctttct ccaccggaga agaagacctc ttcaccgctg
ctctgcgctt ccgcttgctc cgccacaacg gcatcgaaat cagccctgaa
atattcctaa aattcaagga cgagagggga aaattcgacg aatcggacac
gctagggtta ctgagcttgt acgaagcgtc aaatttgggg gttgcaggag
aagaaatatt ggaggaggct atggagtttg cggaggctcg cctgagacgg
tcgctgtcag agccggcggc gccgcttcat ggtgaggtgg cgcaagcgct
agatgtgccg aggcatctga gaatggcgag gttggaagcg agacgattca
tcgagcagta tggtaaacag agcgatcatg atggagatct tttggagctg
gcaattttgg attataatca agttcaggct caacaccaat ccgaactcac
tgaaataatc aggtggtgga aggagctcgg tttggtggat aagttgagtt
ttgggcgaga cagaccattg gagtgctttt tgtggaccgt ggggctcctc
ccagagccca agtattcgag cgttagaata gagttggcga aagccatctc
tattctctta gtgatcgatg atattttcga tacctatgga gagatggatg
acctcatcct cttcaccgat gcaattcgaa gatgggatct tgaagcaatg
gaggggctcc ctgagtacat gaaaatatgc tacatggcgt tgtacaatac
caccaatgaa gtatgctaca aagtgctcag ggatactgga cggattgtcc
tccttaacct caaatctacg tggatagaca tgattgaagg tttcatggag
gaagcaaaat ggttcaatgg tggaagtgca ccaaaattgg aagagtatat
agagaatgga gtgtccacgg caggagcata catggctttt gcacacatct
tctttctcat aggagaaggt gttacacacc aaaattccca actcttcacc
caaaaaccct accccaaggt cttctccgcc gccggccgca ttcttcgcct
ctgggatgat ctcggaaccg ccaaggaaga gcaagagcga ggagatctgg
cttcgtgcgt gcagttattt atgaaagaga agtcgttgac ggaagaggag
gcaagaagtc gcatttggaa agagataaaa ggattatgga gggatctgaa
tggggaactg gtctacaaca agaatttgcc gttatccata atcaaagtcg
cacttaacat ggcgagagct tctcaagttg tgtacaagca cgatcaagac
acttattttt caagcgtaga caattatgtg gatgccctct tcttcactca
ataa
```

Figure 1

```
ger syn :                                                                                    MSCARITVTLPYRSAKTSIQRGITHYPALIRPRFSA-CT-----PLASAMPLSSTPLINGDNSQRKNTRQHMESSSKRREYLLEETTR  : 83
4S-lim  : MALKVLSVATQMAIPSNLITCLQPSHFKSSPKLLSSTNSSSRSRLRVYCS---SSQLTTERRSGNYNPSRWDVNFIQSLLSDYKEDKHIVIRASELVTLVK  : 97
1,8-cin : MSSLIMQVVIPKPAKIFHNNLFSVISKRHRFSTTITTRGGRWAHCSLQMGNEIQTGRRTGGYQPTLWDFSTIQLFDSEYKEEKHLMRAAGMIAQVN     : 96 ger syn : KLQRNDTESVEKLKLIDNIQQLGIGYYFEDAINAVIRSPFSTGE-------------EDLFTAALRFRLLRHNGIEISPEIFLKFKDERG--KFDE----SDTLG   : 169
4S-lim  : MELEKETDQIRQLELIDDLQRMGLSDHFQNEFKEILSSIYLDHHYYKNPFPKERDLYSTSLAFRLLREHGFQVAQEVFDSFKNEEG-EFKESISDDTRG   : 196
1,8-cin : MLLQEEVDSIQRLELIDDLLRRLGISCHFEDREIVELLNSKYYTNN------EIDESDLYSTALRFKLLRQYDFSVSQREVFDCFKNDKGTDEKPSLVDDTRG   : 190 ger syn : LLSLYEASNIGVAGEEILEEAMEFAEARIRRSLSEP--AAPLHGEVAQALDVPRHLRMARLEARRFIEQYGKQSDHDGDLLELAILDYNQVAQHQSELT    : 267
4S-lim  : LLQLYEASFLITEGETTLESAREFATKFLEEKVNEGGVDGDLLITRIAYSLDIPLHWRIKRPNAPVWIEWYRKKRPDMNPVLELAILDLNIVQAFQEELK : 296
1,8-cin : LLQLYEASFISAQGEETIHLARDFATKFTLHKRVLVD-KDINLLSSIERALELPTHWRVQMPNARSFIDAYKRRPDMNPTVLELAKLDFNMVQAFQQELK  : 289 ger syn : EIIRWWKELGLVDKISFGRDRPLECFLWTVGLLPEPKYSSVRIELAKAISILLVIDDIFDTYGEMDDIIILFTDAIRRWDLEAMEGLPEYMKICYMALYNT : 367
4S-lim  : ESFRWRNTGFVEKLPFARDLVECYFWNTGIIEPRQHASARIMWGKVNALITVIDDIDYDYGTLEELEQFTDLIRRWDINSIDQLPDYMQLCFLAINNE   : 396
1,8-cin : EASRWWNSTGLVHELPEVRDRIVECYYWTGVERREHGYERIMLTKINALVTTIDDVFDIYGTLEELQLFTTAIQRWDIESMKQLPPYMQICYLALFNF    : 389 ger syn : TNEVCXKVLRDTGRIVLLNEKSTWIDMIEGFMEBEAKWFNGGSAPKLEEYIENGVSTAGAYMAFAHIFELIGEGVTHQNSQLFTQKPYPKVFSAAGRILRL  : 467
4S-lim  : VDDTSYDVMKEKGVNVIPYLRQSWVDLADKVMVEARWFYGGHKPSLEEYLENSWQSISGPCMLTHIFFRVTDSFTKET--VDSLYKYHDLVRWSSFVLRI  : 494
1,8-cin : VNEMAVDTLRDKGFNSTPYLRKAWVDLIVESYLIEAKMYYMGHKPSLEAKMYYMGHKPSIEEYMKNSWISIGIGFPILSHLFFRLTDSIEEED--AESMHKYHDIVRASCTILRL : 487 ger syn : WDDLGTAKEEQERGDLASCVQLFMKEKSLTEEEARSRILEEIKGLWRDLNGELVYN-KNLPLSIIKVAINMARASQVVYKHDQDTY---FSSVDNYVDAL  : 563
4S-lim  : ADDLGTSVEEVSRGDVPKSLQCYMSDYNASEAEARKHVKWLIFAEVWKKMNAERVSKDSPFGKDFIGCAVDLGRMAQLMYHN-GDGHGTQHPIIHQQMTRT  : 593
1,8-cin : ADDMGTSLDEVERGDVPKSVQCYMNEKNASEEEAREHVRSLIDQTWKMMNKEMMT--SSFSKYFVQVSANLARMAQMIYQHESDGFGMQHSLVNKMLRGL  : 585 ger syn : FFTQ   : 567
4S-lim  : LFEPFA : 599
1,8-cin : LFDRYE : 591
```

Figure 2

GERANIOL SYNTHASE, METHODS OF PRODUCTION AND USES THEREOF

CROSS-REFERENCE TO RELATED APPLICATIONS

This application is a continuation of U.S. patent application Ser. No. 10/582,549 filed on Feb. 4, 2008 now U.S. Pat. No. 7,704,716, which is a National Stage of International Application No. PCT/US2004/040321 filed on Dec. 2, 2004, and which claims priority to U.S. Provisional Application No. 60/528,202 filed on Dec. 10, 2003. The entire disclosures of the above applications are incorporated herein by reference.

STATEMENT OF GOVERNMENTAL SUPPORT

This invention was made with Governmental Support Work Order Award No. IS-3322-02C, USDA NRICGP 2001-35318-10006, N awarded by the U.S. Department of Agriculture. The U.S. Government has certain rights in this invention.

FIELD OF THE INVENTION

The present invention relates to Geraniol synthase (GES), a key enzyme in the production of the monoterpene aroma compound geraniol. More specifically, the present invention relates to nucleic acid sequences coding for GES from sweet basil plant species as well as to vectors containing the sequences, to host cells containing the sequences and to methods of producing recombinant GES, its products, and uses thereof.

BACKGROUND OF THE INVENTION

Flavors and aromas, many of which originate from plants, have always had an important role in human culture. Ancient cultures cultivated and prized plants for their nutritional value as well as for their flavor, aroma and medicinal properties. However, the development of commercial large-scale agriculture in western civilizations resulted in emphasizing commercial/marketing interests in plant production, such as long shelf life, physical appearance and yield. The content of secondary metabolites, i.e. metabolites which do not have a defined metabolic role and presence of which is restricted to specific tissues, were often overlooked, although they significantly affect the nutritional value and aroma. Nowadays, there is growing awareness to healthy and flavorful plant products. Physically appealing but flavorless and aroma-less fruit is perceived as "synthetic", while scented fruit is perceived as more "natural". There is increasing public interest to "return" the natural flavor and aroma to fruits, emphasizing the importance of elucidating the relevant biosynthetic pathways, enzymes, genes and regulatory mechanisms involved. Cosmetic and food industries also seek natural aroma and flavors.

The monoterpene geraniol, which is emitted from flowers, notably roses (Rao et al 2000) and herbs (Mockute et al 1999) of many species, has an important role in their overall flavor and aroma. The mixture of geraniol's oxidation products, geranial and neral, also called citral, imparts a "lemon" flavor, and lemongrass (Singh Sangwan et al 1993), ginger (Miyazawa et al 1998), and some varieties of sweet basil (Grayer et al 1996) such as "Sweet Dani" are particularly rich in citral (Morales et al 1997). However, much is still lacking in the study of the physiological, biochemical and genetic regulation of the production of aroma compounds within the plants. Terpenoids are found in all plant species and have diverse physiological roles such as phytoalexins, pest deterrents and toxins, growth regulators, pollinator attractants, photosynthetic pigments and electron acceptors (Gershenzon and Croteau, 1993; Chappell, 1995; McGarvey and Croteau, 1995). For example, U.S. Pat. No. 6,258,602 discloses the isolation and bacterial expression of a sesquiterpene synthase cDNA clone from peppermint that produces the aphid alarm pheromone E-betafarnesene.

Monoterpenes are also one of the important groups of secondary metabolites involved in herb, fruit and flower aromas. While the backbones of the biosynthetic pathways leading to production of monoterpenes are ubiquitous to all plant species, the composition of terpenes often differs dramatically between species or even varieties leading to the diversity of aroma and flavors among herbs and fruits. This diversity seems to stem mainly from the specific composition and expression of the key-enzymes in the biosynthetic pathway, the terpene synthases, and additional downstream modification enzymes. Homology analysis revealed that while sequence conservation was not high among terpene synthases of different plant species, discrete conserved domains were present suggesting significant structural and functional similarity (Back and Chappell, 1995; Steele et al., 1998). These conserved domains have been the basis for isolation of a number of terpene synthases encoding genes from a variety of plant species using degenerate-primer based RT-PCR (Bohlmann et al., 1998a, 1998b, 1999; Steele et al., 1998).

Geraniol is likely to be synthesized from geranyl diphosphate (GDP), the universal precursor of all monoterpenes. Two types of enzymatic reactions have been hypothesized to lead to geraniol synthesis from GDP, either a phosphate-based or a monoterpene-based catalysis. However, in the absence of purified and characterized geraniol synthase, the question of whether GES employs a similar mechanism to the one used by other monoterpene synthases remained unsolved. This state of research limits the ability of the agricultural, food and cosmetic industries to use natural herb aromas, which are highly desirable in products of these industries.

Thus, there is a recognized need for, and it would be highly advantageous to have specific compounds involved in the regulation of herbal aroma pathways, and more advantageous to have isolated polynucleotides and enzymes capable of producing said aromas.

SUMMARY OF THE INVENTION

The present invention relates to a key enzyme in the production of the monoterpene geraniol, an aroma compound found mainly in flower and herb species.

The present invention provides a novel type of the enzyme geraniol synthase (GES), which is involved in the terpene biosynthetic pathway converting geranyl diphosphate (ODP) to geraniol. According to one aspect, the monoterpene synthase is GES. The present invention also provides polynucleotide sequences encoding the GES, including recombinant DNA molecules. The present invention further provides vectors and host cells, including vectors comprising the polynucleotides of the present invention, host cells engineered to contain the polynucleotides of the present invention and host cells engineered to express the polynucleotides of the present invention. Thus, the present invention provides methods for (i) expressing the recombinant monoterpene synthase, specifically GES, to facilitate the production, isolation and purification of significant quantities of recombinant GES, or of its primary and secondary products for subsequent use; (ii) expressing or enhancing the expression of a monoterpene synthase, specifically GES, in microorganisms or in plants;

and (iii) regulating the expression of a monoterpene synthase, specifically GES, in an environment where such regulation of expression is desired for the production of the enzyme and for producing the enzyme products and derivatives thereof.

The present invention further provides polynucleotide sequences encoding monoterpene synthase, specifically GES, for use in a variety of methods and techniques known to those skilled in the art of molecular biology, including, but not limited to the use as hybridization probes, as oligomers for PCR, for chromosome and gene mapping, and the like.

The present invention also provides methods for using monoterpene synthase enzymatic products, specifically geraniol, in the agricultural, cosmetic and food industries.

According to one aspect, the present invention provides monoterpene synthase characterized in that it converts geranyl diphosphate (GDP) to geraniol, and polynucleotides encoding same.

According to one embodiment, the present invention provides an isolated polynucleotide comprising a genomic, complementary or composite polynucleotide sequence encoding a GES, said GES being capable of converting GDP to geraniol.

According to one embodiment, the present invention provides an isolated polynucleotide comprising a nucleic acid sequence selected from the group consisting of:
(a) the nucleic acid sequence of SEQ ID NO:1 (FIG. 1);
(b) the complement of SEQ ID NO:1;
(c) a nucleic acid sequence which is at least 90% homologous to SEQ ID NO:1; and
(d) a nucleic acid sequence capable of hybridizing either (a) or (b).

According to one another embodiment, the present invention provides a polynucleotide comprising a nucleic acid sequence encoding a GES comprising the amino acid sequence of SEQ ID NO:2 (FIG. 2).

According to one embodiment, the present invention provides an isolated polynucleotide comprising a nucleic acid sequence encoding a GES which is at least 60%, preferably at least 70%, more preferably at least 80% or more, most preferably at least 90% or 100% homologous (similar+identical amino acids) to the amino acid sequence set forth in SEQ ID NO:2.

According to yet another embodiment, the present invention provides an isolated polynucleotide comprising a nucleic acid sequence encoding a GES comprising the amino acid sequence of SEQ ID NO:2, or fragments, derivatives and analogs thereof. The present invention also provides an isolated polynucleotide comprising a nucleic acid sequence which hybridizes to the polynucleotide encoding GES comprising the amino acid sequence of SEQ ID NO:2 or fragments, derivatives and analogs thereof. The present invention further provides an isolated polynucleotide comprising a nucleic acid sequence which is complementary to the polynucleotide encoding a GES comprising the amino acid sequence of SEQ ID NO:2 and fragments, derivatives and analogs thereof.

According to one another embodiment, the present invention provides a polypeptide having GES activity, said activity being characterized by converting geranyl diphosphate (GDP) to geraniol.

According to one embodiment, the present invention provides a GES having the amino acid sequence of SEQ ID NO:2.

According to another embodiment, the present invention provides a polypeptide which is at least 60%, preferably at least 70%, more preferably at least 80% or more, most preferably at least 90% or 100% homologous (similar+identical amino acids) to the amino acid sequence set forth in SEQ ID NO:2, said polypeptide is a GES.

According to one embodiment, the GES of the present invention is originated from herb species, specifically from oranges basil cultivar "Sweet Dani".

According to another aspect, the present invention provides methods for the production, isolation and purification of the GES, as well as of the products of its enzymatic activity.

According to one embodiment, the present invention provides an expression vector comprising a nucleic acid sequence encoding a GES.

According to another embodiment, the present invention provides an expression vector comprising a nucleic acid sequence selected from the group consisting of:
(a) the nucleic acid sequence of SEQ ID NO:1;
(b) the complement of SEQ ID NO:1;
(c) a nucleic acid sequence which is at least 90% homologous to SEQ ID NO:1; and
(d) a nucleic acid sequence capable of hybridizing either (a) or (b).

According to yet another embodiment, the present invention provides an expression vector comprising a polynucleotide sequence encoding a GES having SEQ ID NO:2.

According to further embodiment, the present invention provides an expression vector comprising a polynucleotide sequence encoding a GES which is at least 60%, preferably 70%, more preferably 80% or more, most preferably at least 90% or 100% homologous to SEQ ID NO:2.

According to one another embodiment the present invention provides a host cell containing the expression vector of the present invention. The present invention further provides a method for producing recombinant GES, the method comprising a) culturing the host cell containing the expression vector comprising at least a fragment of the polynucleotide sequence encoding GES under conditions suitable for the expression of the enzyme; and b) recovering the enzyme from the host cell culture. According to a further embodiment the present invention provides a method for producing significant amounts of geraniol, the method comprising a) culturing the host cell containing an expression vector comprising at least a fragment of the polynucleotide sequence encoding GES under conditions suitable for the expression and activity of the enzyme; and b) recovering geraniol from the host cell culture.

The geraniol produced within a host cell according to the present invention can serve as a substrate for producing additional compounds by enzymes present in the host cell active downstream to GES in the terpene biosynthesis pathway. Such compounds are designated herein as "geraniol metabolites".

According to one embodiment the present invention provides a method for producing significant amounts of geraniol metabolites downstream in the terpene biosynthesis pathway the method comprising a) culturing the host cell containing an expression vector comprising at least a fragment of the polynucleotide sequence encoding GES under conditions suitable for the expression and activity of the GES; and b) recovering geraniol metabolites from the host cell culture.

According to one preferred embodiment the geraniol metabolites are geranial and neral.

Prokaryotic as well as eukaryotic expression systems may be utilized for the production of GES and its product geraniol, and geraniol metabolites downstream in the terpene biosynthesis pathway. Both systems comprise the necessary elements for posttranslational modification enabling the proper activity of the enzyme, as well as the necessary substrates for the synthesis of geraniol and the enzymes for the synthesis of downstream geraniol metabolites.

According to yet another aspect the present invention provides a prokaryotic organism in which significant amounts of geraniol are synthesized.

According to one embodiment, the present invention provides a prokaryotic organism comprising a polynucleotide sequence encoding a GES stably integrated into its genome.

According to one embodiment, the present invention provides a prokaryotic organism comprising a nucleic acid sequence selected from the group consisting of SEQ ID NO:1, the complement of SEQ ID NO:1, a nucleic acid sequence which is at least 90% homologous to SEQ ID NO:1, a nucleic acid sequence capable of hybridizing to SEQ ID NO:1 and a nucleic acid sequence capable of hybridizing to the complement of SEQ ID NO:1, stably integrated into its genome. According to another embodiment, the present invention provides a prokaryotic organism comprising a polynucleotide sequence encoding a GES having the amino acid sequence of SEQ ID NO:2 stably integrated into its genome.

According to yet another embodiment the present invention provides a prokaryotic organism comprising a polynucleotide sequence encoding a GES comprising amino acid sequence which is at least 60%, preferably at least 70%, more preferably at least 80% or more, most preferably at least 90% or 100% homologous to SEQ ID NO:2 stably integrated into its genome.

According to yet further embodiment, the present invention provides a prokaryotic organism comprising a polynucleotide encoding GES stably integrated into its genome, said prokaryotic organism produces geraniol.

According to one preferred embodiment, the prokaryotic organism is selected from the group consisting various bacteria; preferably, the prokaryotic organism is *E. coli*.

According to yet another aspect, the present invention provides geraniol and geraniol metabolites obtained by the methods of the present invention for industrial uses.

According to one embodiment, the present invention provides geraniol and geraniol metabolites obtained by the methods of the present invention for use in a product selected from the group consisting of agricultural, cosmetic, and food products.

According to another embodiment, the geraniol metabolites are geranial and neral.

The present invention is explained in greater detail in the description, figures and claims that follows.

BRIEF DESCRIPTION OF THE FIGURES

FIG. 1 shows the nucleotide sequence of GES, SEQ ID NO:1.

FIG. 2 shows the relatedness of GES to other terpene synthases. Amino acid sequence of basil GES (SEQ ID NO:2) is compared with two most similar terpene synthases for which a function is known, 1,8, cineol synthase from *Salvia officinalis* (SEQ ID NO:3) and 4S-limonene synthase from *Mentha spicata* (SEQ ID NO:4). Residues identical in at least two of the proteins at a given position are shaded. Lines above the sequence indicate the tryptic peptides of GES identified by ESI-MS/MS. The RRX8W motif (which is absent in GES) is double-underlined. Serine[35] and methionine[44] in GES are underlined and in bold.

(FIG. 4A) Extraction from young leaves. (FIG. 4B) Extraction from glands. (FIG. 4C) Extraction of product after an enzyme assay with crude protein extract incubated with GDP. Labeled peaks are: 1: Internal standard included for quantification, 2: β-caryophyllene, 3: methyl chavicol, 4: neral, 5: Germacrene D, 6: geranial, 7: α-farnesene, 8: nerol, 9: geraniol.

Unlabeled peaks in (C) are not terpenes, and are found in the protein crude extract regardless of whether GDP is included in the assay.

Figure 5:
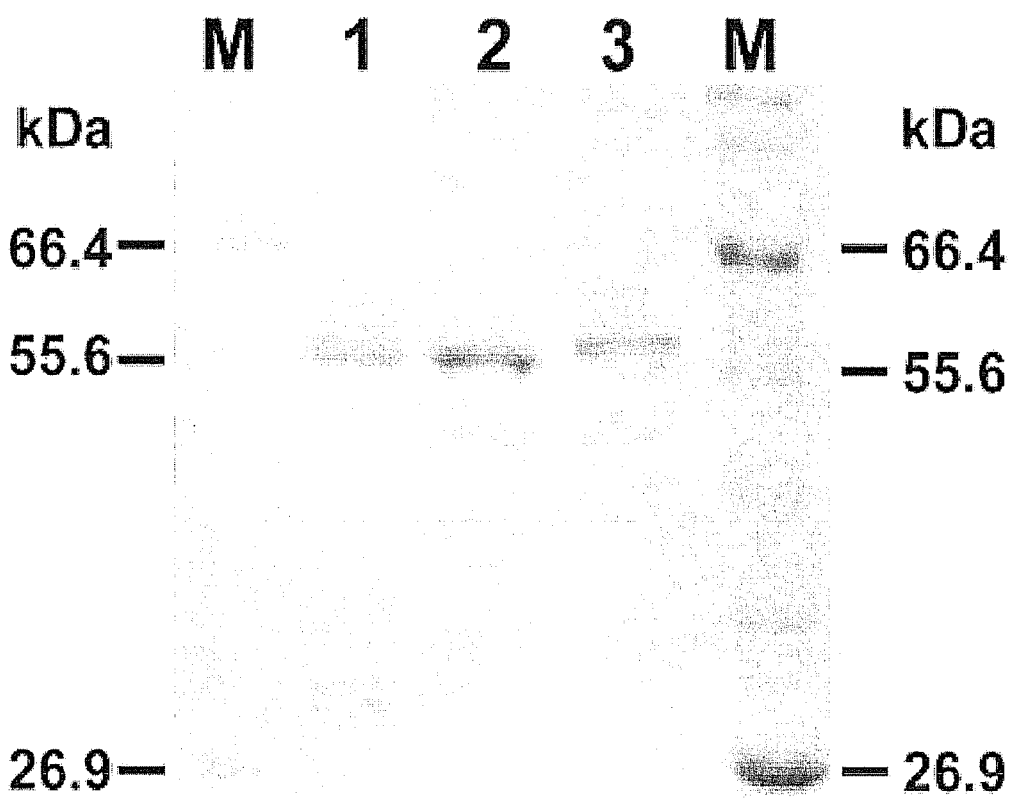

FIG. 5 shows SDS-PAGE analysis of purified basil GES from the leaf glands and from *E. coli* expression system. Lane 1, purified GES after Superose-12 size-exclusion chromatography. Lane 2, MonoQ-purified truncated GES (starting from Met44) produced in *E. coli*. Lane 3, MonoQ-purified truncated GES (starting from Ser35) produced in *E. coli*. Lanes marked "M" contain molecular weight markers. Gels were stained with Coomassie Blue.

Figure 6:
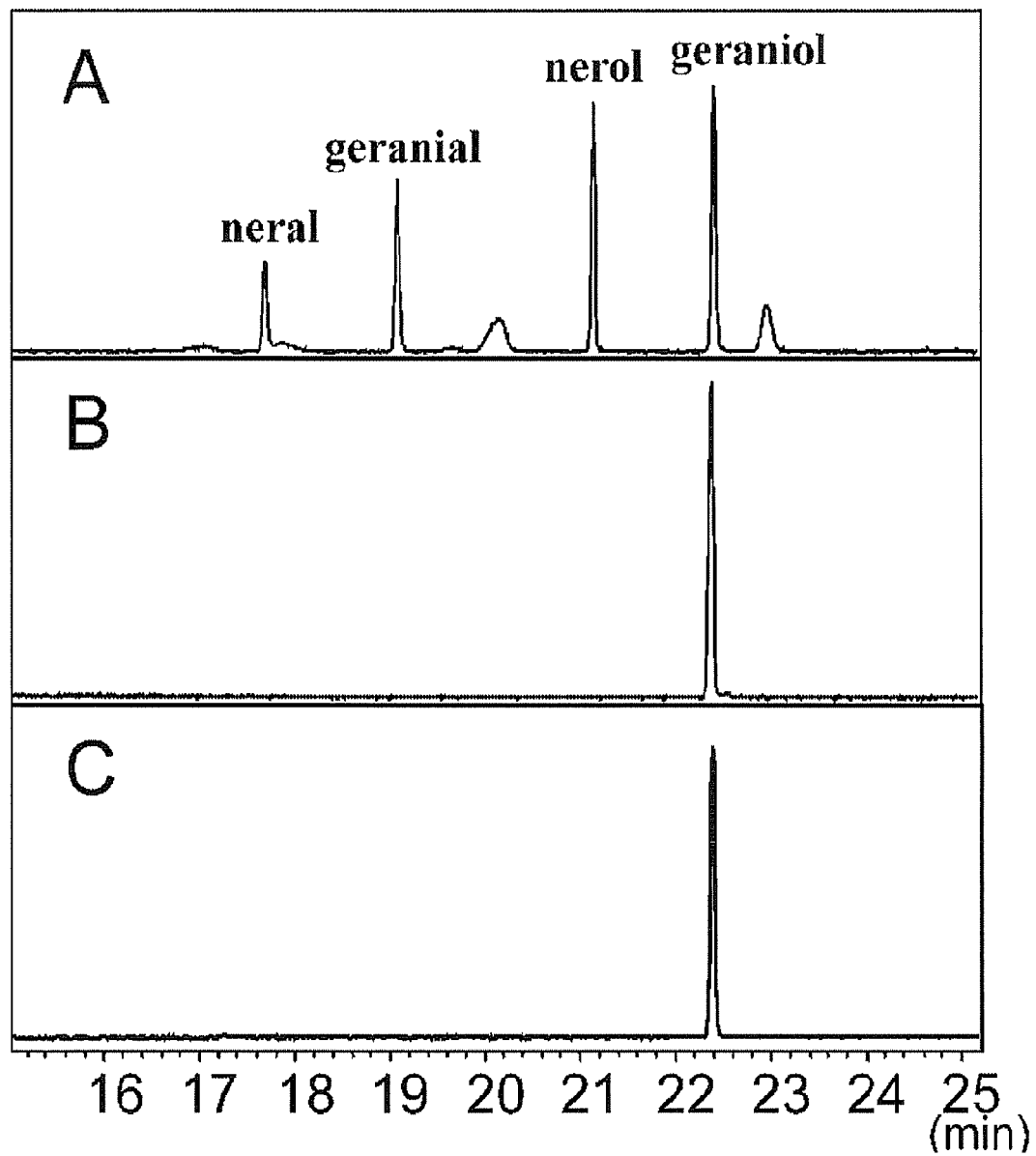

FIG. 6 shows analysis of the products of the reaction catalyzed by purified GES with GDP. (FIG. 6A) Gas chromatographic separation of authentic standards of neral, geranial, nerol, and geraniol. (FIG. 6B) SPME-Gas chromatogram of the reaction solution following catalysis by gland-purified basil GES. Only a single peak was observed, identified as geraniol by MS. (FIG. 6C) SPME-Gas chromatogram of the reaction solution following catalysis by basil GES purified from the *E. coli* expression system. Only a single peak was observed, identified as geraniol by MS.

Figure 7:
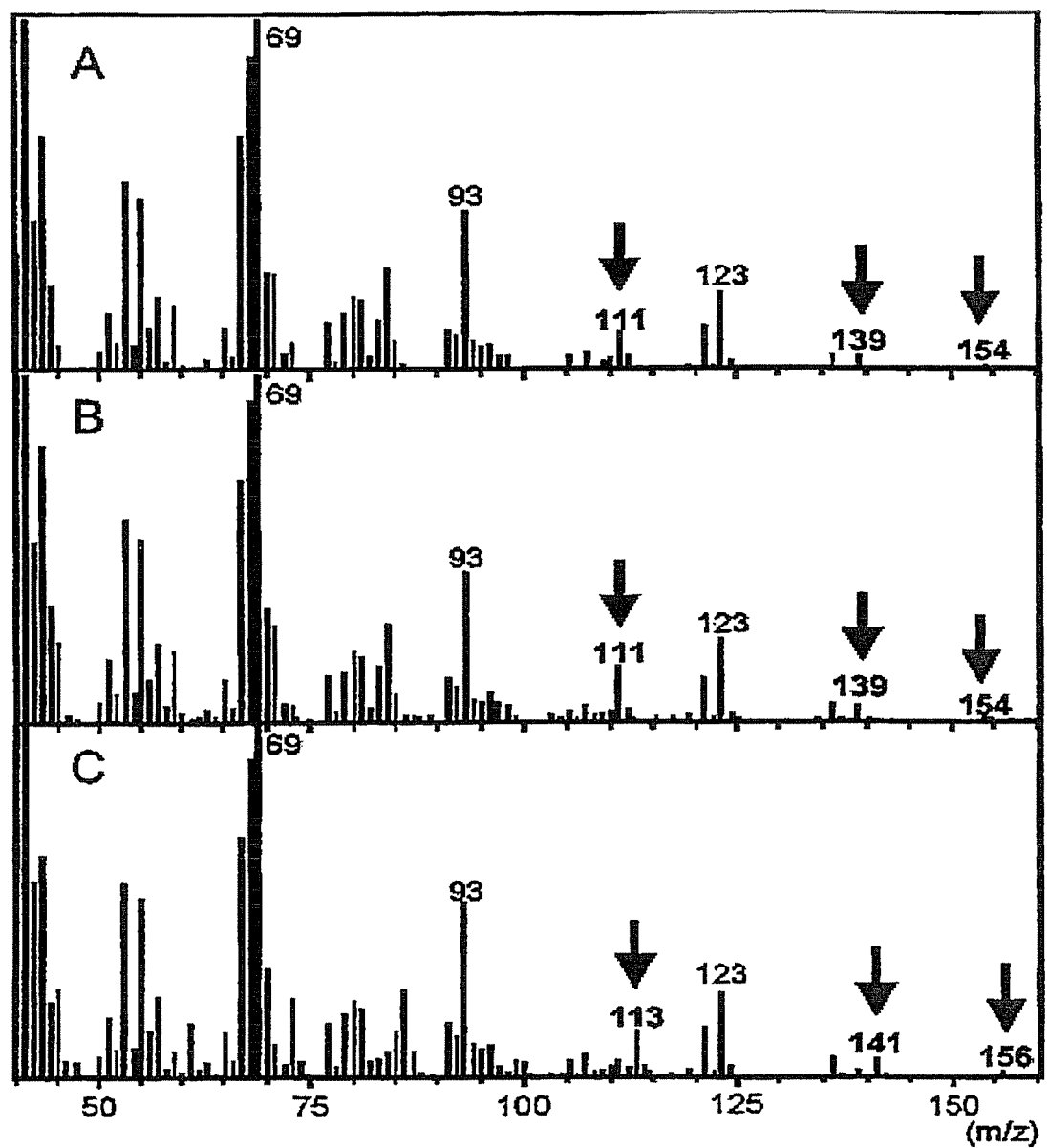

FIG. 7 compares mass spectra of geraniol produced in enzymatic reactions with purified GES in buffers containing either non-isotopic water ($H_2^{16}O$) or $^{18}O$-labeled water ($H_2^{18}O$). (FIG. 7A) Mass spectra of a geraniol standard. (FIG. 7B) Mass spectra of geraniol from a reaction including non-isotopic water ($H_2^{16}O$). (FIG. 7C) Mass spectra of geraniol from a reaction containing $^{18}O$-labeled water ($H_2^{18}O$). Arrows indicate the mass of fragments containing oxygen, 154/156 ($M^+$), 139/141 ($M^+$-$CH_3$), and 111/113 ($M^+$-$C_3H_7$).

Figure 8:
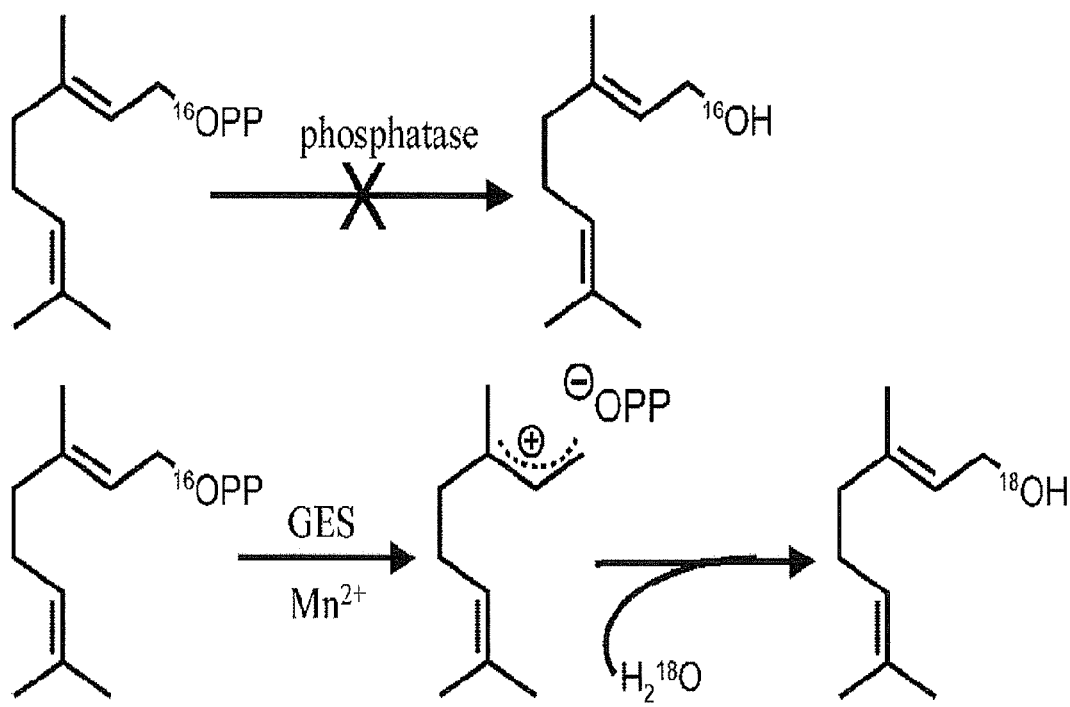

FIG. 8 describes the Reaction mechanism of GES. Geraniol is not generated by phosphatase activity from GDP, but is formed by the addition of a hydroxyl group to a carbocation intermediate.

DETAILED DESCRIPTION OF THE INVENTION

The present invention relates to novel types of monoterpene synthases, specifically to geraniol synthase.

The present invention relates to a key enzyme in the production of the monoterpene geraniol, an aroma compound found mainly in flower and herb species.

The present invention discloses the isolation and characterization of a key gene/enzyme in flower and herb aroma formation: geraniol synthase (GES). Recombinant enzyme activity in-vitro shows a single monoterpene product identified as geraniol.

Definitions

As used herein, the terms "amino acid" and "amino acids" refer to all naturally occurring L-α-amino acids or their residues. The amino acids are identified by either the single-letter or three-letter designations.

As used herein, the term "nucleotide" means a monomeric unit of DNA or RNA containing a sugar moiety (pentose), a phosphate and a nitrogenous heterocyclic base. The base is linked to the sugar moiety via the glycosidic carbon (1' carbon of pentose) and that combination of base and sugar is called a nucleoside. The base characterizes the nucleotide with the four bases of DNA being adenine ("A"), guanine ("G"), cytosine ("C"), thymine ("T") and inosine ("I"). The four RNA bases are A,G,C and uracil ("U"). The nucleotide sequences described herein comprise a line array of nucleotides connected by phosphodiester bonds between the 3' and 5' carbons of adjacent pentoses.

The term "percent identity" means the percentage of amino acids or nucleotides that occupy the same relative position when two amino acid sequences, or two nucleic acid sequences are aligned side by side.

The term "percent similarity" is a statistical measure of the degree of relatedness of two compared protein sequences. The percent similarity is calculated by a computer program that assigns a numerical value to each compared pair of amino acids based on chemical similarity (e.g., whether the compared amino acids are acidic, basic, hydrophobic, aromatic, etc.) and/or evolutionary distance as measured by the minimum number of base pair changes that would be required to convert a codon encoding one member of a pair of compared amino acids to a codon encoding the other member of the pair. Calculations are made after a best fit alignment of the two sequences has been made empirically by iterative comparison of all possible alignments. (Henikoff, S, and Henikoff, J. G., Proc, Nat'l. Acad. Sci. USA 89:10915-10919, 1992).

"Oligonucleotide" refers to short length single or double stranded sequences of deoxyribonucleotides linked via phosphodiester bonds. The oligonucleotides are chemically synthesized by known methods and purified on polyacrylamide gels.

The term "Monoterpene synthase" is used herein to mean an enzyme capable of catalyzing the production of monoterpene from GDP. "Geraniol synthase" (GES) is used herein to mean an enzyme that catalyzes the production of the monoterpene geraniol from GDP.

The terms "alteration", "amino acid sequence alteration", "variant" and "amino acid sequence variant" refer to GES molecules with some differences in their amino acid sequences as compared to GES from specific flowers and herbs, especially GES of the basil cultivar "Sweet Dani" having the amino acid sequence set forth in SEQ ID N0:2. Ordinarily, the variants will possess at least about 70% homology, preferably at least about 80% homology with the above defined GES. The amino acid sequence variants of GES falling within this invention possess substitutions, deletions, and/or insertions at certain positions. Sequence variants of GES may be used to attain desired enhanced enzymatic activity or altered substrate utilization or product distribution. Substitutional GES variants are those that have at least one amino acid residue in the GES sequence set forth in SEQ ID N0:2 removed and a different amino acid inserted in its place at the same position. The substitutions may be single, where only one amino acid in the molecule has been substituted, or they may be multiple, where two or more amino acids have been substituted in the same molecule. Substantial changes in the activity of the GES molecules of the present invention may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the GES molecules of the present invention would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional GES variants are those with one or more amino acids inserted immediately adjacent to an amino acid at a particular position in the amino acid sequence of GES set forth in SEQ ID NO:2. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those where one or more amino acids in the amino acid sequence of GES set forth in SEQ ID N0:2 have been removed. Ordinarily, deletional variants will have one or two amino acids deleted in a particular region of the GES molecule.

The term "biological activity", "biologically active", "activity" and "active" refer to the ability of the monoterpene synthase to convert geranyl diphosphate (GDP) to a group of monoterpenes, of which geraniol is the principle and characteristic monoterpene synthesized by GES.

The terms "DNA sequence encoding", "DNA encoding", "nucleic acid encoding" or "polynucleotide sequence encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

The term "hybridization", as used herein, refers to any process by which a strand of nucleic acid binds with a complementary strand through base pairing.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. to about 25° C. below the melting temperature of the probe). One or more factors may be varied to generate conditions of either low or high stringency.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host. The vector is used to transport the foreign or heterologous DNA into a suitable host cell. Once in the host cell, the vector can replicate independently of or coincidental with the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The terms "transformed host cell," "transformed" and "transformation" refer to the introduction of DNA into a cell.

The cell is termed a "host cell", and it may be a prokaryotic or a eukaryotic cell. Typical prokaryotic host cells include various strains of E. coli. Typical eukaryotic host cells are plant cells, yeast cells, insect cells or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

Novel Monoternene Synthase

According to one aspect, the present invention relates to polynucleotides encoding for monoterpene synthase, specifically GES.

As described herein below, the present invention shows that the only product of geraniol synthase is geraniol, a reaction mechanism which is similar to the reaction mechanism of other terpene synthases. Therefore, a large EST database constructed from the peltate glands of three basil varieties, including Sweet Dani, for potential GES cDNAs, were examined. Two of these cultivars, EMX1 and SW, do not produce geraniol (or citral) but they do produce other monoterpenes, such as 1,8-cineole, linalool, and fenchone. BLAST searches identified 5 different types of cDNA sequences in Sweet Dani with sequence homology to known terpene synthases, but only one type of sequence was significantly unique to Sweet Dani, encoding a protein that was highly divergent from any terpene synthase-like sequence found in the other cultivars (less than 35% identity), whereas the other four cDNAs encoded proteins that were >90% identical to proteins from the SW and EMXI varieties. A complete cDNA of this sequence, obtained by 5' RACE followed by RT-PCR, contains an open reading frame of 1701 nucleotides that encodes a protein of 567 amino acids (FIG. 1).

According to one embodiment, the present invention provides an isolated polynucleotide comprising a genomic, complementary or composite polynucleotide sequence encoding a GES, said GES being capable of converting GDP to geraniol.

According to one embodiment, the present invention provides an isolated polynucleotide comprising a nucleic acid sequence selected from the group consisting of:
  (a) the nucleic acid sequence of SEQ ID NO:1;
  (b) the complement of SEQ ID NO:1;
  (c) a nucleic acid sequence which is at least 90% homologous to SEQ ID N0:1; and
  (d) a nucleic acid sequence capable of hybridizing either (a) or (b).

According to one another embodiment, the present invention provides a polynucleotide comprising a nucleic acid sequence encoding a GES comprising the amino acid sequence of SEQ ID NO: 2.

According to one embodiment, the present invention provides an isolated polynucleotide comprising a nucleic acid sequence encoding a GES which is at least 60%, preferably at least 70%, more preferably at least 80% or more, most preferably at least 90% or 100% homologous (similar+identical amino acids) to the amino acid sequence set forth in SEQ ID NO: 2.

According to another embodiment, the present invention provides a polynucleotide encoding a GES comprising the amino acid sequence of SEQ ID N0:2, or fragments, derivatives and analogs thereof. The present invention also provides a polynucleotide which hybridizes under stringent conditions to the polynucleotide encoding GES comprising the amino acid sequence of SEQ ID NO: 2 or fragments, derivatives and analogs thereof. The present invention further provides a polynucleotide which is complementary to the polynucleotide encoding a GES comprising the amino acid sequence of SEQ ID NO:2 or fragments, derivatives and analogs thereof.

The isolation of cDNA encoding GES permits the development of efficient expression systems for this functional enzyme; provides useful tools for examining the developmental regulation of geraniol biosynthesis; permits investigation of the reaction mechanism(s) of this unique enzyme and permits the transformation of a wide range of organisms in order to introduce geraniol biosynthesis de novo, or to modify endogenous geraniol biosynthesis.

According to another aspect, the present invention relates to polypeptides having monoterpene synthase activity, specifically GES activity, i.e., said polypeptides convert GDP to monoterpene, specifically geraniol.

From the complete deduced amino acid sequence of the GES cDNA clone (SEQ ID NO: 2, FIG. 2), GES shares the highest sequence similarity to monoterpene synthases from Lamiaceae species (Wise et al 1998; Colby et al 1993).

Figure 3:
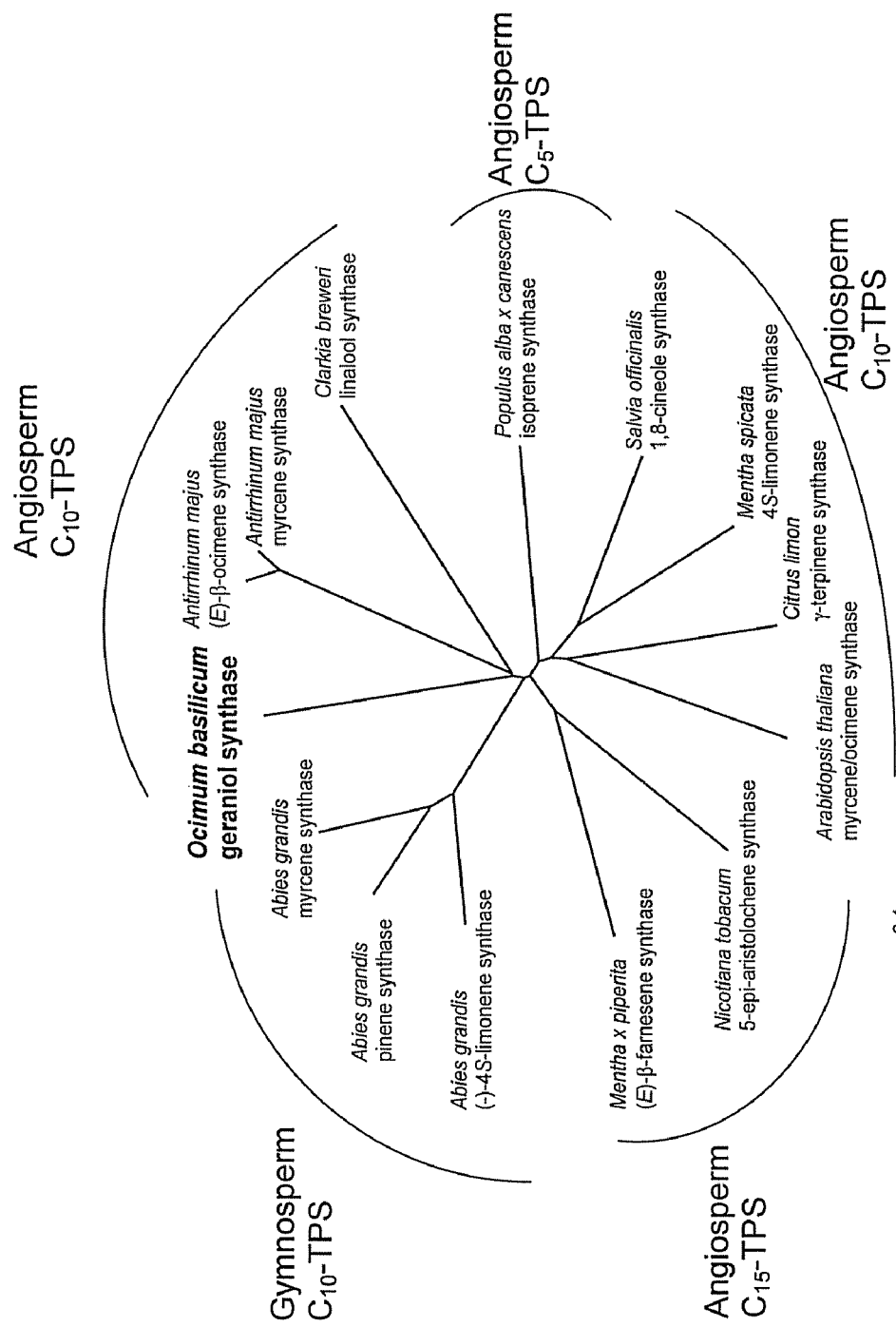
FIG. 3 shows the position of Geraniol synthase on the phylogenetic map of terpene synthases. Alignment was performed using Clustalx and phylogenetic tree was drawn using TreeView.

A phylogenetic analysis of the deduced amino-acid sequence of GES, suggests that GES occupies a highly divergent branch of the terpene synthase family, but it most likely shares a most recent common origin with the Snapdragon ocimene and Myrcene synthases and to C. breweri linalool synthase, all terpene synthases catalyzing the formation of acyclic monoterpenes (FIG. 3) (ClustalX and Treeview software, Thompson, 1997 and Page, 1996, respectively).

According to one another embodiment, the present invention provides a polypeptide having GES activity, said activity being characterized by converting geranyl diphosphate (GDP) to geraniol.

According to one embodiment, the present invention provides a GES having the amino acid sequence of SEQ ID NO:2.

According to another embodiment, the present invention provides a polypeptide which is at least 60%, preferably at least 70%, more preferably at least 80% or more, most preferably at least 90% or 100% homologous (similar+identical amino acids) to the amino acid sequence set forth in SEQ ID NO:2, said polypeptide is a GES.

In addition to the native GES amino acid sequence, sequence variants produced by deletions, substitutions, mutations and/or insertions are intended to be within the scope of the invention. The GES amino acid sequence variants of this invention may be constructed by mutating the DNA sequence that encodes the wild-type synthase, such as by using techniques commonly referred to as site-directed mutagenesis. Nucleic acid molecules encoding the GES of the present invention can be mutated by a variety of PCR techniques well known to one of ordinary skill in the art. See, e.g., 'PCR Strategies", M. A. Innis, D. H. Gelfand and J. J. Sninsky, eds., 1995, Academic Press, San Diego, Calif. (Chapter 14); "PCR Protocols: A Guide to Methods and Applications", M. A. Innis, D. H. Gelfand, J. J. Sninsky and T. J. White, eds., Academic Press, NY (1990).

By way of non-limiting example, the two-primer system utilized in the Transformer Site-Directed Mutagenesis kit from Clontech, may be employed for introducing site-directed mutants into the GES gene of the present invention. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of E. coli. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subjoining or generation of single-stranded phagemids. The tight linkage of the two mutations and the subsequent linearization of unmutated plasmids result in high mutation efficiency and allow minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed to confirm that no other alterations in the sequence have occurred (e.g., by band shift comparison to the unmutagenized control).

In the design of a particular site directed mutagenesis, it is generally desirable to first make a non-conservative substitution (e.g., Ala for Cys, His or Glu) and determining if activity is greatly impaired as a consequence. The properties of the mutagenized protein are then examined with particular attention to the kinetic parameters of $K_m$ and $k_{cat}$ as sensitive indicators of altered function, from which changes in binding and/or catalysis per site may be deduced by comparison to the native enzyme. If the residue is demonstrated to be important by activity impairment, or knockout, then conservative substitutions can be made, such as Asp for Glu to alter side chain length, Ser for Cys, or Arg for His. For hydrophobic segments, it is commonly size that is usefully altered, although aromatics can also be substituted for alkyl side chains. Changes in the normal product distribution can indicate which step(s) of the reaction sequence have been altered by the mutation. Modification of the hydrophobic pocket can be employed to change binding conformations for substrates.

Other site directed mutagenesis techniques might also be employed with the nucleotide sequences of the invention. For example, restriction endonuclease digestion of DNA followed by ligation may be used to generate deletion variants of GES, as described in section 15.3 of Sambrook et al. (Molecular Cloning: A Laboratory Manual, 2nd Ed., Cold Spring Harbor Laboratory Press, New York, N.Y. 1989). A similar strategy may be used to construct insertion variants, as described in section 15.3 of Sambrook et al., supra.

Oligonucleotide-directed mutagenesis may also be employed for preparing substitution variants of this invention. It may also be used to conveniently prepare the deletion and insertion variants of this invention. This technique is well known in the art as described, for example, by Adelman et al. (DNA 2:183 1983); Sambrook et al., supra; "Current Protocols in Molecular Biology", 1991, Wiley (NY), F. T. Ausubel, R. Brent, R. E. Kingston, D. D. Moore, J. D. Seidman, J. A. Smith and K. Struhl, eds.

Generally, oligonucleotides of at least 25 nucleotides in length are used to insert, delete or substitute two or more nucleotides in the nucleic acid molecules encoding GES of the invention. An optimal oligonucleotide will have 12 to 15 perfectly matched nucleotides on either side of the nucleotides coding for the mutation. To mutagenize nucleic acids encoding the native GES of the invention, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the native synthase inserted in the vector, and the second strand of DNA encodes the mutated form of the synthase inserted into the same vector. This heteroduplex molecule is then transformed into a suitable host cell.

Mutants substituted with more than one amino acid may be generated in one of several ways. If the amino acids are located close together in the polypeptide chain, they may be mutated simultaneously using one oligonucleotide that codes for all of the desired amino acid substitutions. If however, the amino acids are located in some distance from each other (e.g., separated by more than ten amino acids) it is more difficult to generate a single oligonucleotide that encodes all of the desired changes. Instead, one of two alternative methods may be employed. In the first method, a separate oligonucleotide is generated for each substituted amino acid. The oligonucleotides are ten annealed to the single-stranded template DNA simultaneously, and the second DNA strand synthesized from the template will encode all of the desired amino acid substitutions. An alternative method involves two or more rounds of mutagenesis to produce the desired mutant. The first round is as described for the single mutants: native GES DNA is used for the template, an oligonucleotide encoding the first desired amino acid substitution is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and the second rounds of mutagenesis. The mutagenized DNA can then be used as a template in a third round of mutagenesis, and so on.

According to one currently preferred embodiment, the GES of the present invention is originated from basil species, specifically from "Sweet Dani" cultivar.

Sweet basil (*Ocimum basilicum*) such as "Sweet Dani" is particularly rich in citral. Over 99% of the monoterpenes present in "Sweet Dani" comprises of geraniol, nerol, geranial and neral. The accumulation of these monoterpenes during the maturation of the leaves was analyzed. Younger leaves had the highest levels of monoterpenes and the levels got progressively lower as the leaves mature and expand (table 1).

TABLE I

Levels of geranial, neral, geraniol and nerd in leaves of different age in the basil "Sweet Dani" cultivar.

|  | Geranial | Neral | Geraniol | Nerol |
| --- | --- | --- | --- | --- |
| mmall leaves | 1.80 ± 0.31[a] | 0.92 ± 0.20 | 0.14 ± 0.08 | .05 ± 0.03 |
| Medium Leaves | 1.17 ± 0.12 | 0.57 ± 0.02 | 0.4 ± 0.02 | 0.02 ± 0.01 |
| Large Leaves | 0.83 ± 0.42 | 0.38 ± 0.13 | 0.01 ± 0.00 | 0.01 ± 0.00 |

[a]mg/g fresh leaves ± S.D.

According to another aspect, the present invention provides methods for the production, isolation and purification of the GES according to the present invention, as well as of the products of its enzymatic activity.

A gene encoding GES may be incorporated into any organism capable of synthesizing terpenes, or cell culture derived thereof.

The geraniol-encoding gene may be incorporated into the organism for a variety of purposes, including but not limited to production of GES; production of geraniol; production of products downstream to geraniol; and production or modification of flavor and aroma compounds.

According to one embodiment, the present invention provides an expression vector comprising a nucleic acid sequence encoding a GES.

According to another embodiment, the present invention provides an expression vector comprising a nucleic acid sequence selected from the group consisting of:
(a) the nucleic acid sequence of SEQ ID NO:1;
(b) the complement of SEQ ID NO:1;
(c) a nucleic acid sequence which is at least 90% homologous to SEQ ID NO:1; and
(d) a nucleic acid sequence capable of hybridizing either (a) or (b).

According to yet another embodiment, the present invention provides an expression vector comprising a polynucleotide sequence encoding a GES having SEQ ID NO:2.

According to further embodiment, the present invention provides an expression vector comprising a polynucleotide sequence encoding a GES which is at least 60%, preferably 70%, more preferably 80% or more, most preferably at least 90% or 100% homologous to SEQ ID NO:2.

Vectors of various types may be used in the practice of the present invention. A specific vector type is used according to the host cell in which expression is desired, as is known to a person with ordinary skill in the art, and as described herein below. The vector usually has a replication site, marker genes that provide phenotypic selection in transformed cells, one or more promoters, and a polylinker region containing several restriction sites for insertion of foreign DNA. For example, plasmids typically used for transformation of E. coli include pBR322, pUC 18, pUC 19, pUCI18, pUC1 19, and Bluescript M13, all of which are described in sections 1.12-1.20 of Sambrook et al., supra. These vectors contain genes coding for ampicillin and/or tetracycline resistance, which enables cells transformed with these vectors to grow in the presence of these antibiotics. However, many other suitable vectors, harboring different genes encoding for selection markers are available as well. The construction of suitable vectors containing DNA encoding replication sequences, regulatory sequences, phenotypic selection genes and the GES DNA of interest are prepared using standard recombinant DNA procedures. Isolated plasmids and DNA fragments are cleaved, tailored, and ligated together in a specific order to generate the desired vectors, as is well known in the art (see, for example, Sambrook et al., supra).

According to yet another embodiment the present invention provides a host cell containing the expression vector of the present invention. The present invention further provides a method for the production of recombinant GES, the method comprising a) culturing the host cell containing the expression vector comprising at least a fragment of the polynucleotide sequence encoding GES under conditions suitable for the expression of the GES; and b) recovering GES from the host cell culture.

The host cell may be transformed with the expression vector according to the present invention by using any known method for the insertion of foreign nucleic acid sequences into a prokaryotic or eukaryotic host cell. The transformation process results in the expression of the inserted DNA such as to change the recipient cell into a transformed, genetically modified or transgenic cell.

Potential cDNA encoding GES were examined by RT-PCR and cloning of full length cDNAs into the pCRT7/CT-TOPO TA vector (Invitrogen, Carlsbad, Calif.). These constructs were expressed in the E. coli expression system, and the resulted proteins (64.9 kDa) were tested for GES activity. Since the monoterpenes synthases N-terminus serves as a transit peptide, which is cleaved after the protein is inserted into the organelle (Bohlmami at al 1998). Constructs encoding truncated GES proteins missing the first 34 or 43 amino acids (the exact location of the cleavage site has not yet been determined with certainty) were also constructed in either pCRT7/CT-TOPO TA vector or a pET-11a vector. These constructs were expressed in the E. coli expression system, and the resulted proteins (61.2 and 60.2 kDa, respectively) were tested for GES activity. Conditions were worked out to obtain substantial amounts of active gene products.

Recombinant GES proteins were harvested from E. coli cells (with the constructs), and were purified using several chromatographic steps (table 2). The purified proteins supplemented with $Mn^{2+}$ were found to convert radiolabeled GDP into geraniol (SPME-Gas chromatogram) as exemplified herein below (FIG. 6C). The present invention thus discloses the conversion of radiolabeled GDP into a putative monoterpene geraniol by the activity of GES gene product.

TABLE 2

Purification of GES from gland of basil "Sweet Dani" cultivar

| | Total activity (ptat) | Protein (mg) | Specific activity (pkat/mg) | Purification | Yield (%) |
|---|---|---|---|---|---|
| Crude | 3874.9 | 23.77 | 163.0 | 1 | 100 |
| DE-53 | 1225.7 | 2.71 | 153.0 | 2.8 | 31.7 |
| Mono Q | 265.5 | 0.43 | 617.7 | 3.8 | 6.9 |
| Superose12 | 337.2 | 0.05 | 6244.2 | 38.3 | 8.7 |

According to a further embodiment the present invention provides a method for producing significant amounts of geraniol, the method comprising a) culturing the host cell containing an expression vector comprising at least a fragment of the polynucleotide sequence encoding GES under conditions suitable for the expression and activity of the GES; and b) recovering geraniol from the host cell culture.

According to yet another embodiment the present invention provides a method for producing significant amounts of geraniol metabolites downstream in the terpene biosynthesis pathway. According to one preferred embodiment the downstream geraniol metabolites are geranial and neral.

Figure 4:
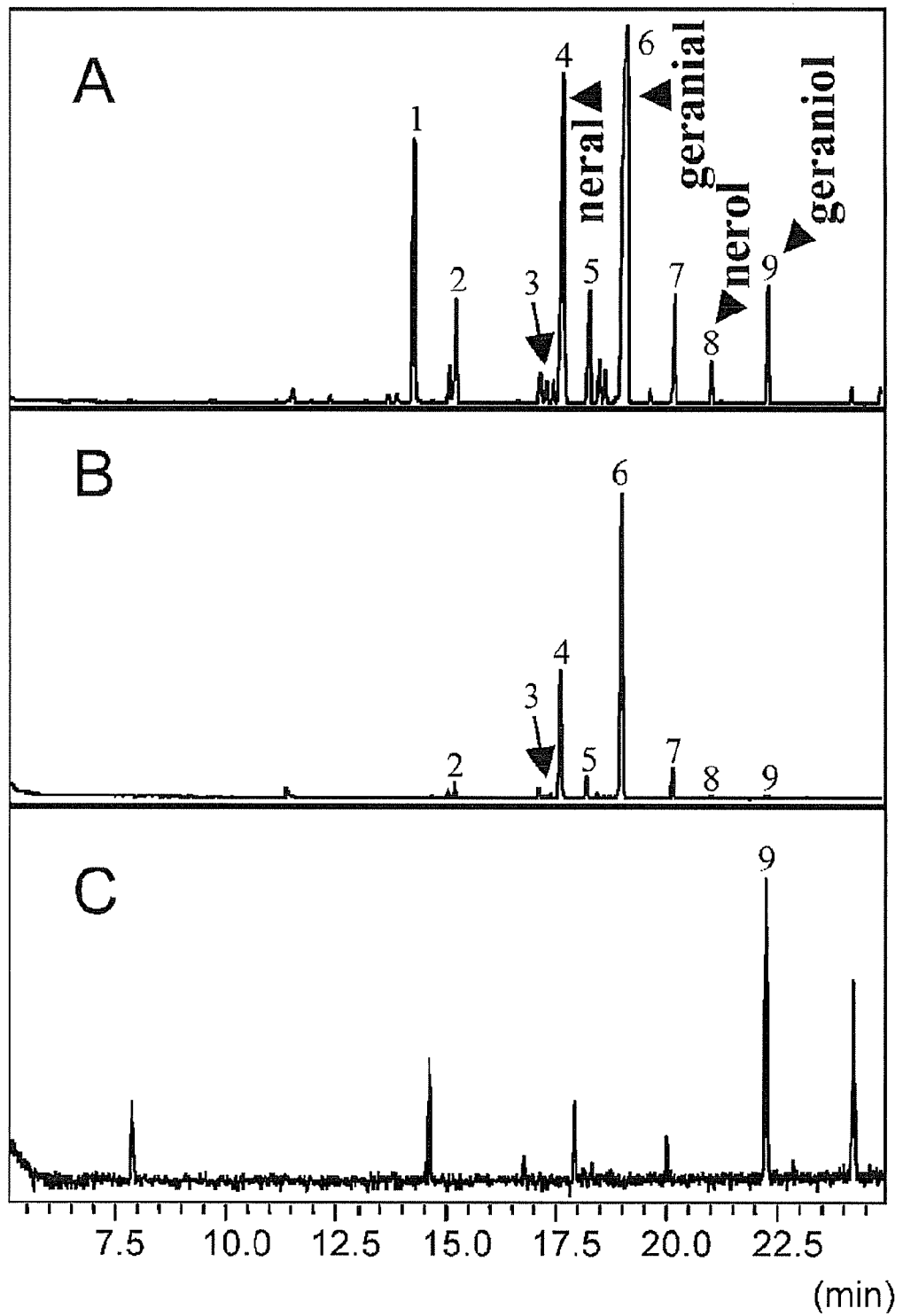
FIG. 4 shows identification of monoterpenes extracted from leaves and glands of sweet basil cultivar "Sweet Dani" and produced by a crude protein extract from the glands by GC-MS.

The mixture of geraniol with his oxidation products, geranial and neral (also called citral), imparts a "lemon" flavor, and lemongrass, ginger, and some varieties of sweet basil such as "Sweet Dani" are particularly rich in citral (together with neral they constitute >70% of total essential oil terpenes) (FIG. 4A). Therefore, geraniol and his metabolites are of interest to the food and cosmetic industry.

According to yet another aspect the present invention provides a prokaryotic or eukaryotic organism in which significant amounts of geraniol are synthesized.

According to one embodiment, the present invention provides a prokaryotic organism comprising a polynucleotide sequence encoding a GES stably integrated into its genome.

According to one embodiment, the present invention provides a prokaryotic organism comprising a nucleic acid sequence selected from the group consisting of SEQ ID NO:1, the complement of SEQ ID NO:1, a nucleic acid sequence which is at least 90% homologous to SEQ ID NO:1, a nucleic acid sequence capable of hybridizing to SEQ ID NO:1 and a nucleic acid sequence capable of hybridizing to the complement of SEQ ID NO: 1, stably integrated into its genome. According to another embodiment, the present invention provides a prokaryotic organism comprising a polynucleotide sequence encoding a GES having the amino acid sequence of SEQ ID NO:2 stably integrated into its genome.

According to yet another embodiment the present invention provides a prokaryotic organism comprising a polynucleotide sequence encoding a GES comprising amino acid sequence which is at least 60%, preferably at least 70%, more preferably at least 80% or more, most preferably at least 90% or 100% homologous to SEQ ID N0:2 stably integrated into its genome.

According to further embodiment, the present invention provides a prokaryotic organism comprising a polynucleotide encoding GES stably integrated into its genome, said prokaryotic organism produces geraniol.

According to one preferred embodiment, the prokaryotic organism is selected from the group consisting of various bacteria. Preferably, the prokaryotic organism is selected from *E. coli* strains.

As is known to a person skilled in the art, many bacterial strains are suitable as host cells for the over-expression of monoterpenes according to the present invention, including *E. coli* strains and many other species and genera of prokaryotes including bacili such as *Bacillus subtilis*, other enterobacteriaceae such as *Salmonella typhimurium* or *Serratia marcesans*, and various *Pseudomonas* species. Prokaryotic host cells or other host cells with rigid cell walls are preferably transformed using the calcium chloride method as described in section 1.82 of Sambrook et al., supra. Alternatively, electroporation may be used for transformation of these cells. Prokaryote transformation techniques are known in the art, e.g. Dower, W. J., in Genetic Engineering, Principles and Methods, 12:275-296, Plenum Publishing Corp., 1990; Hanahan et al., Meth. Enzymol., 204:63 1991.

Although geraniol was reported to be emitted from flowers of many species, notably roses (Rao et al 2000; Antonelli et at 1997; Bayrak et al 1994), and from vegetative tissues of many herbs (Mockute et at 1999; Charles et al 1992; Vieira et at 2001; Mallavarapu et al 1998), the present invention discloses for the first time a gene encoding GES. Accordingly, to the best of our knowledge, there are no other known genes encoding GES from any other Genus.

According to yet another aspect, the present invention provides geraniol and geraniol metabolite produced downstream in the monoterpene biosynthesis pathway obtained by the methods of the present invention for industrial uses.

According to one embodiment, the present invention provides geraniol and geraniol metabolites obtained by the methods of the present invention for use in a product selected from the agricultural, cosmetic, and food products.

According to another embodiment, the products downstream to geraniol are geranial and neral.

The principles of the invention, disclosing novel monoterpene synthase, polynucleotides encoding same, methods of productions and methods for use may be better understood with reference to the following non-limiting examples.

EXAMPLES

Plant Material

Seeds for "Sweet Dani" were obtained from a local nursery. They were sown in Horticultural vermiculite and put in the growth chamber until germination. One week after germination, each seedling was transplanted into 500 ml pot containing Sunshine Mix no. 1 polling soil and grown in a greenhouse under constant illumination.

Volatile Oil Extraction from Leaves and Glands

Basil leaves were categorized into three sizes, small (0.5-1.5 cm), medium (1.5-3 cm), and large (3-4 cm). Two hundred milligram of each leaves were added to liquid N2 and ground by mortar and pestle. The powder was soaked in 2 ml MTBE (methyl t-butyl ether) containing 0.1 mg linalool as internal standard (linalool was used because the "Sweet Dani" cultivar does not contain linalool) and extracted for 2 hours at room temperature in 5 ml glass vials with tightly sealed rubber septa caps. The MTBE upper layer, which included the volatile oil, was removed and placed into another vial and concentrated to 200 µl under gentle N2 gas flow for GC-MS analysis. Data points were obtained in triplicates.

Volatile oils were extracted from the glands of young leaves with a stretched glass pipette (Gang et al 2001).

GC-MS Analysis of Plant Volatiles

A Shimadzu QP-5000 system (Shimadzu, Columbia, Md.) equipped with Shimadzu GC-17 gas chromatograph was used for GC-MS analysis of volatile compounds. Separation was performed on DB-WAX (30 m×0.32 mm i.d.×0.25 am film thickness, J&W Scientific, Folsom, Calif.) capillary column with electron impact mode (1.4 kV). However, some nonpolar compounds eluted with the solvent peak in the DB-WAX column, and their separation was achieved on CP-5 column (30 m×0.32 mm i.d.×1 µm film thickness, Alltech Associates Inc., Deerfield, Ill.). The oven temperature for DB-WAX methods was held at 60% for 2 mm and raised to 220° C. at 4° C./min with the injector set at 220° C. and the interface set at 240° C. The GC condition for CP-5 method was same with previous report (Gang et al 2001). Ultrapure helium was used as the carrier gas at a rate of 1.3 ml/min. Samples (2 µl) were injected by the Shimadzu AOC-17 Autoinjector. Eluted compounds were identified by comparing their retention time and mass fragmentation patterns with standard compounds.

Example 1

GES Enzyme Assays

GES activity was assayed by incubating 5 µl of the enzyme sample in a final volume of 50 µl buffer containing 50 mM Hepes-KOH, pH 8.0, 1 mM DTE, 0.5 mM MnCI2, 20 mM MgCl2, 10% glycerol and 54 µM [1-3H]-GDP (specific activity 20 Ci/mol, American Radiolabeled Chemicals, St. Louis, Mo.). After incubation for 30 mm at 320 C, 160 µl hexane was added to the tube, and vortexed briefly and centrifuged to separated the phases. The hexane layer was directly placed into a scintillation vial containing 2 ml of nonaqueous scintillation fluid (Econo-Safe, Research Products International, Mount Prospect Ill.). This extraction procedure was repeated twice and the total hexane phase was counted by Liquid Scintillation counter (LS-6500 model, Beckman Coulter, Fullerton, Calif.). Boiled enzyme extracts were used as controls.

Identification of Enzymatic Products

GES enzyme assays were also performed by adding 100 µl of enzyme solution with 900 µl assay solution containing 54 µM non-radioactive GDP (Echelon Research Laboratories, Salt Lake City, Utah) and the same buffer described above. The reactions were carried out in an 8 mL DuPont autosampler vial with a white solid-top polypropylene cap (Alltech, Deerfield, Ill.). After letting the reaction proceed for 2-4 hr at 32° C., the liberated compounds were collected with a solid-phase microextraction (SPME) device PDMS-100 with a polydimethylsiloxane fiber (Supelco, Bekkefonte, Pa.) by inserting the fiber into the tube and leaving it in for 20 mim at 42° C. After this incubation step, the solid-phase microextraction fiber was directly injected into the GC-MS.

Example 2

Terpene Synthase Assays with $^{18}$O-Labeled Water

Assays in buffer containing 18O-labeled water were carried out in 2 ml glass vials with screw cap of PTFE/Silicone Septa (Supelco, Bellefonte, Pa.) by the addition 20 µl of purified enzyme (app. 1 µg protein) to 180 µl assay solution that contained 20 µl 10× assay buffer with 150 µl H2 18O (95% atom, Icon Service, Summit, N.J.) and 10 µl of 5.4 mM GDP. The final concentration of H2 18O in this assay solution was 71.3%. This solution was incubated for 2 hr at 320 C, and cooled down on ice, then extracted with 200 µl pentane. After concentration to 50 µl, 2 µl of this solution was injected to GC-MS system. To compare the mass spectra pattern, a pentane extract of the product from a reaction in which normal water (H2 16O) was used was also analyzed.

Phosphatase Activity Assay

Phosphatase activity was measured (Harnandez et al 1996) with the following modification: Assay samples were prepared by incubating 50 µl of enzyme solution in a final volume of 400 µl assay buffer containing 2 mM p-nitrophenyl phosphate as substrate. The buffer composition was the same as with the GES assay (but without GDP). After incubation for 1 h at room temperature, the reaction was stopped by adding of 700 µl of 0.2 M Na2CO3. The yellow color generated from the hydrolysis of p-nitrophenyl phosphate was measured at 420 nm in a spectrophotometer (Beckman DU530, Fullerton, Calif.). Phosphatase activity was calculated using a standard curve for p-nitrophenol. For the purified enzyme, this assay was scaled down ten-fold.

Example 3

GES Purification

All purification steps were carried out at 40 C unless stated otherwise. Glands were isolated from approx. 300 g of Sweet Dani basil (Gang et al 2001), with a total yield of 4 ml of resuspended glands. The gland preparation was diluted 10:1 (V/V) in ice-cold enzyme extraction buffer (100 mM BisTris-HCl, pH 7.5, 10 mM DTE, 5 mM Na2S2O4, 2% (w/v) PVPP, 10% glycerol), and sonicated on ice, with rest intervals for cooling down, until gland cells were completely lysed. After centrifugation for 20 mm at 10,000 g, the supernatant (39 ml) was loaded onto a DEAE-cellulose column (10 mL of DE53, Whatman, Fairfield, N.J.) installed in a Pharmacia FPLC apparatus and pre-equilibrated with a solution containing 50 mM Tris-HCl, pH 7.5, 10% glycerol, and 10 mM β-mercaptoethanol (buffer A). After elution of unbound material from the column with 25 ml of buffer A, GES activity was eluted with 200 ml of a linear gradient from 0 to 1 M KCl in buffer A. The flow rate was 1.0 ml/min, and 3 ml fractions were collected and then assayed for GES activity. The fractions with the highest GES activity were pooled (KCl concentration of 255-435 mM, a total of 38 ml), and dialyzed in buffer A for 4 hr to remove KCl. This dialysis step did not result in any decrease in GES activity. The enzyme solution was subsequently loaded onto strong anion exchange column (Mono Q, 0.5 cm×6.0 cm, Pharmacia Biotech, Piscataway, N.J.) pre-equilibrated with buffer A. After washing off the unbound material with 2 ml of buffer A, GES was eluted with 50 mL of a linear gradient 0-700 mM KCl in buffer A at 0.5 ml/min, and 1 ml fractions were collected. The highest GES activity was detected in the 2 ml fraction containing 294 mM KCl. To this fraction was added octyl glucoside (final concentration of 5 mM), and the enzyme was concentrated in an Ultrafree-4 centrifugal device (Millipore, Bedford, Mass.) to a total volume of 2000. The concentrated enzyme solution was loaded onto a size exclusion column (10 mm×300 mm) packed with Superose 12 (Pharmacia) and active fraction was isocratically eluted with 100 mM KCl in Buffer A at 0.2 ml/min. Fractions (0.5 ml each) were collected and protein purity was examined by SDSPAGE gel electrophoresis followed by Coomassie Brilliant Blue or silver staining of the gel. The protein concentrations were measured by the Bradford method or by staining intensity on SDS-PAGE compared with BSA concentration standards.

Molecular Mass Estimation

Partially purified GES was run on a size exclusion column under the same conditions used during the purification procedure, except that 0.25 ml fractionations were collected instead, and fractions were assayed for GES activity. A standard curve was obtained by plotting the Ve/V0 of the standard proteins against the log of the molecular weight. The protein standards used included cytochrome C (12.4 kDa), carbonic anhydrase (29 kDa), ovalbumin (45 kDa), bovine serum albumin (66 kDa), alcohol dehydrogenase (from equine liver, 80 kDa), and alcohol dehydrogenase (from yeast, 141 kDa). The subunit molecular weight was estimated by SDS-PAGE performed on 10% polyacrylamide gel and calibrated with molecular weight standard in the range of 14-212 kDa (New England BioLabs, MA).

Example 4

Characterization of GES Properties

The pH optimum for GES activity was determined using three buffer systems. Reaction was carried out in 50 mM Bis-Tris buffer ranging from pH 6.0 to 7.0, 50 mM Tris-HCl buffer ranging pH 7.0 to 9.0, and 50 mM glycine-NaOH buffer ranging from pH 9.0 to 10.0. Temperature stability of GES was determined by incubating GES in temperatures ranging from 4 to 650 C for 30 mm and then chilling the samples on ice, followed by enzyme assays at 320 C. To determine the kinetic parameters of GES, the enzyme was diluted to the appropriate concentration and incubation time was set for 30 mm at 320 C. In determining the Km value for GDP. Mn2+ concentration was set at a saturated level and GDP concentration was changed from 0.5 pM to 108 µM with 10 different data points. The Km value for Mn2+ was measured at saturated GDP levels, and Mn2± concentration was changed from 4 µM to 1000 µM with 9 data points. Lineweaver-Burk plots were made to obtain the Km value.

Example 5

ESI-MS/MS Analysis of Purified GES

Mass spectrometric analysis of the purified GES was carried out in the Proteomics Core Facility of the Southwest Environmental Health Sciences Center and Arizona Cancer Center, at The University of Arizona. Proteins were first separated by SDS-PAGE, as described above, stained lightly with Coomassie brilliant blue R250, excised from the gel and digested with trypsin (Shevchenko et al 1996). Extracted peptides were analyzed by liquid chromatography-tandem mass spectrometry (LC-MS/MS) using a ThermoFinnigan LCQ Classic quadrupole ion trap mass spectrometer (San Jose, Calif.) equipped with a Michrom MAGIC2002 HPLC (Auburn, Calif.) and a nanospray ion source (University of Washington). Peptides were loaded onto 10-cm capillaries (365 µm O.D.×100×m I.D.; packed with 5-6 cm of Vydac C18 material) that were pulled to 3-5 um tips using a Suffer Instruments P2000 capillary puller (Novato, Calif.). Peptides were eluted at a flow rate of 200-300 nL·min-1 into the mass spectrometer using reversed phase solvent conditions (Shevchenko et al 1996). Tandem MS spectra of peptides were analyzed with the TurboSequest program to assign peptide sequences to the spectra (Eng et al 1994). TurboSequest analyses were performed against the sweet EST databases housed at the Arizona Genomics Institute at the University of Arizona. The non-identified spectra were further analyzed by ExPASy peptide mass program (available online at us.expasy.orgltools/peptide-mass.html) for the calculated tryptic peptide masses from full length GES cDNA.

Example 6

Isolation of GES cDNA5 and Expression in E. coli

A basil cv. Sweet Dani peltate gland EST database containing 3,200 unique sequences was developed at the Arizona Genomics Institute and the Arizona Genomics Computational Laboratory at the University of Arizona, using a cDNA library constructed from gland mRNA5 (Gang et al 2001). BLAST searches revealed numerous ESTs with sequence similarity to terpene synthases. Potential cDNA5 encoding GES were examined by RT-PCR cloning of full length cDNA5 into the pCRT7/CT-TOPO TA vector (Invitrogen, Carlsbad, Calif.), expressing these constructs in the E. coli expression system, and testing the resulting proteins for activity with GDP (described in Chen et al 2003). Constructs encoding truncated GES proteins missing the first 34 or 43 amino acids were also constructed (using the method described in Chen et al 2003) in either pCRT7/CT-TOPO TA vector or a pET-11a vector. After harvesting recombinant GES proteins from E. coli cells, the proteins were purified using the same method employed in the purification of GES from basil glands.

Example 7

Sequence Analysis

Alignment of multiple protein sequences was performed using the ClustalX program (Thompson et al 1997). Sequence relatedness by the neighbor-joining method was determined using the protocol included in the ClustalX package. The phylogenic tree was drawn using the TREEVIEW program available online at taxonomy.zoolOgy.gla.ac.uk/rOd/treeview.html (Page a all 996)).

The invention claimed is:

1. An isolated polynucleotide that encodes a polypeptide with at least 90% identity to SEQ ID NO: 2, the polynucleotide encoding a geraniol synthetase (GES) capable of converting geranyl diphosphate to geraniol.

2. The isolated polynucleotide of claim 1, wherein the isolated polynucleotide encodes a polypeptide with 100% identity to SEQ ID NO: 2.

3. The isolated polynucleotide of claim 1, wherein the isolated polynucleotide encodes a polypeptide that is missing the first 34 to 43 amino acids of SEQ ID NO: 2.

4. An expression vector comprising the polynucleotide according to claim 1.

5. A host cell comprising the expression vector according to claim 4.

6. A method for producing a polypeptide, the method comprising:

culturing the host cell according to claim 5 under conditions suitable for the expression of the polypeptide; and
recovering the polypeptide from the host cell culture.

7. A prokaryotic organism comprising a polynucleotide according to claim 1 stably integrated into its genome.

8. An isolated polynucleotide comprising a nucleic acid sequence that is at least 90% identical to SEQ ID NO: 1 or the complementary sequence thereof, where the polynucleotide encodes a geraniol synthetase (GES) capable of converting geranyl diphosphate to geraniol.

9. The isolated polynucleotide of claim 8, wherein the nucleic acid sequence is SEQ ID NO: 1 or the complementary sequence thereof.

10. The isolated polynucleotide of claim 8, wherein the nucleic acid sequence is SEQ ID NO: 1 missing the first 34 to 43 codons or the complementary sequence thereof.

* * * * *

UNITED STATES PATENT AND TRADEMARK OFFICE
CERTIFICATE OF CORRECTION

| | | |
|---|---|---|
| PATENT NO. | : 8,124,375 B2 | Page 1 of 1 |
| APPLICATION NO. | : 12/702019 | |
| DATED | : February 28, 2012 | |
| INVENTOR(S) | : Eran Pichersky et al. | |

It is certified that error appears in the above-identified patent and that said Letters Patent is hereby corrected as shown below:

Title Page, No. 75, Inventors, Third Inventor's Address, "Efraim Lewinsohn, Timrat, IL (US)" should be --Efraim Lewinsohn, Timrat (IL)--.

Column 3, line 57, after "According to" delete "one".

Column 4, line 30, after "According to" delete "one".

Column 5, line 34, after "consisting" insert --of--.

Column 9, line 49, after "According to" delete "one".

Column 10, line 28, after "According to" delete "one".

Column 10, line 50, "'PCR" should be --"PCR--.

Column 14, line 6, "at al" should be --et al.--.

Column 15, line 40, both occurrences of "et at" should be --et al.--.

Column 16, line 49, "separated" should be --separate--.

Column 17, line 1, "mim" should be --min--.

Column 18, line 6, "2000" should be --200 μl--.

Column 19, line 4, "100×m I.D." should be --100 pm I.D.--.

Column 19, line 5, "3-5 um" should be --3-5 μm--.

Signed and Sealed this
Third Day of July, 2012

David J. Kappos
*Director of the United States Patent and Trademark Office*

SEQUENCE LISTING

<160> NUMBER OF SEQ ID NOS: 4

<210> SEQ ID NO 1
<211> LENGTH: 1704
<212> TYPE: DNA
<213> ORGANISM: Ocimum basilicum
<300> PUBLICATION INFORMATION:
<301> AUTHORS: Iijima,Y., Gang,D.R., Lewinsohn,E. and Pichersky,E.
<302> TITLE: Characterization of geraniol synthase from the peltate
       glands of sweet basil
<303> JOURNAL: Plant Physiol.
<304> VOLUME: 134
<305> ISSUE: 1
<306> PAGES: 370-379
<307> DATE: 2004
<308> DATABASE ACCESSION NUMBER: AY362553
<309> DATABASE ENTRY DATE: 2004-08-05
<313> RELEVANT RESIDUES IN SEQ ID NO: (1)..(1704)
<300> PUBLICATION INFORMATION:
<308> DATABASE ACCESSION NUMBER: AY362553
<309> DATABASE ENTRY DATE: 2004-08-05
<313> RELEVANT RESIDUES IN SEQ ID NO: (1)..(1704)

<400> SEQUENCE: 1

```
atgtcttgtg cacggatcac cgtaacattg ccgtatcgct ccgcaaaaac atcaattcaa      60
cggggaatta cgcattaccc cgcccttata cgcccacgct tctctgcttg cacgcctttg     120
gcatcggcga tgcctctaag ttcaactcct ctcatcaacg gggataactc tcagcgtaaa     180
aacacacgtc aacacatgga ggagagcagc agcaagagga gagaatatct gctggaggaa     240
acgacgcgaa aactgcagag aaacgacacc gaatcggtgg agaaactcaa gcttatcgac     300
aacatccaac agttgggaat cggctactat tttgaggacg ccatcaacgc cgtactccgc     360
tcgcctttct ccaccggaga agaagacctc ttcaccgctg ctctgcgctt ccgcttgctc     420
cgccacaacg gcatcgaaat cagccctgaa atattcctaa aattcaagga cgagagggga     480
aaattcgacg aatcggacac gctagggtta ctgagcttgt acgaagcgtc aaatttgggg     540
```

```
gttgcaggag aagaaatatt ggaggaggct atggagtttg cggaggctcg cctgagacgg    600
tcgctgtcag agccggcggc gccgcttcat ggtgaggtgg cgcaagcgct agatgtgccg    660
aggcatctga aatggcgag gttggaagcg agacgattca tcgagcagta tggtaaacag    720
agcgatcatg atggagatct tttggagctg gcaattttgg attataatca agttcaggct    780
caacaccaat ccgaactcac tgaaataatc aggtggtgga aggagctcgg tttggtggat    840
aagttgagtt tgggcgaga cagaccattg gagtgctttt tgtggaccgt ggggctcctc    900
ccagagccca gtattcgag cgttagaata gagttggcga agccatctc tattctctta     960
gtgatcgatg atattttcga tacctatgga gagatggatg acctcatcct cttcaccgat   1020
gcaattcgaa gatgggatct tgaagcaatg gaggggctcc ctgagtacat gaaaatatgc   1080
tacatggcgt tgtacaatac caccaatgaa gtatgctaca agtgctcag ggatactgga    1140
cggattgtcc tccttaacct caaatctacg tggatagaca tgattgaagg tttcatggag   1200
gaagcaaaat ggttcaatgg tggaagtgca ccaaaattgg aagagtatat agagaatgga   1260
gtgtccacgg caggagcata catggctttt gcacacatct tctttctcat aggagaaggt   1320
gttacacacc aaaattccca actcttcacc caaaaaccct accccaaggt cttctccgcc   1380
gccggccgca ttcttcgcct ctgggatgat ctcggaaccg ccaaggaaga gcaagagcga   1440
ggagatctgg cttcgtgcgt gcagttattt atgaaagaa gtcgttgac ggaagaggag    1500
gcaagaagtc gcattttgga agagataaaa ggattatgga gggatctgaa tggggaactg   1560
gtctacaaca gaatttgcc gttatccata atcaaagtcg cacttaacat ggcgagagct   1620
tctcaagttg tgtacaagca cgatcaagac acttattttt caagcgtaga caattatgtg   1680
gatgccctct tcttcactca ataa                                          1704
```

<210> SEQ ID NO 2
<211> LENGTH: 567
<212> TYPE: PRT
<213> ORGANISM: Ocimum basilicum

<400> SEQUENCE: 2

```
Met Ser Cys Ala Arg Ile Thr Val Thr Leu Pro Tyr Arg Ser Ala Lys
 1               5                  10                  15

Thr Ser Ile Gln Arg Gly Ile Thr His Tyr Pro Ala Leu Ile Arg Pro
            20                  25                  30

Arg Phe Ser Ala Cys Thr Pro Leu Ala Ser Ala Met Pro Leu Ser Ser
        35                  40                  45

Thr Pro Leu Ile Asn Gly Asp Asn Ser Gln Arg Lys Asn Thr Arg Gln
    50                  55                  60

His Met Glu Glu Ser Ser Ser Lys Arg Arg Glu Tyr Leu Leu Glu Glu
65                  70                  75                  80

Thr Thr Arg Lys Leu Gln Arg Asn Asp Thr Glu Ser Val Glu Lys Leu
                85                  90                  95

Lys Leu Ile Asp Asn Ile Gln Gln Leu Gly Ile Gly Tyr Tyr Phe Glu
            100                 105                 110

Asp Ala Ile Asn Ala Val Leu Arg Ser Pro Phe Ser Thr Gly Glu Glu
        115                 120                 125

Asp Leu Phe Thr Ala Ala Leu Arg Phe Arg Leu Leu Arg His Asn Gly
    130                 135                 140

Ile Glu Ile Ser Pro Glu Ile Phe Leu Lys Phe Lys Asp Glu Arg Gly
145                 150                 155                 160

Lys Phe Asp Glu Ser Asp Thr Leu Gly Leu Leu Ser Leu Tyr Glu Ala
                165                 170                 175
```

```
Ser Asn Leu Gly Val Ala Gly Glu Glu Ile Leu Glu Glu Ala Met Glu
            180                 185                 190

Phe Ala Glu Ala Arg Leu Arg Arg Ser Leu Ser Glu Pro Ala Ala Pro
        195                 200                 205

Leu His Gly Glu Val Ala Gln Ala Leu Asp Val Pro Arg His Leu Arg
    210                 215                 220

Met Ala Arg Leu Glu Ala Arg Arg Phe Ile Glu Gln Tyr Gly Lys Gln
225                 230                 235                 240

Ser Asp His Asp Gly Asp Leu Leu Glu Leu Ala Ile Leu Asp Tyr Asn
                245                 250                 255

Gln Val Gln Ala Gln His Gln Ser Glu Leu Thr Glu Ile Ile Arg Trp
            260                 265                 270

Trp Lys Glu Leu Gly Leu Val Asp Lys Leu Ser Phe Gly Arg Asp Arg
        275                 280                 285

Pro Leu Glu Cys Phe Leu Trp Thr Val Gly Leu Leu Pro Glu Pro Lys
    290                 295                 300

Tyr Ser Ser Val Arg Ile Glu Leu Ala Lys Ala Ile Ser Ile Leu Leu
305                 310                 315                 320

Val Ile Asp Asp Ile Phe Asp Thr Tyr Gly Glu Met Asp Asp Leu Ile
                325                 330                 335

Leu Phe Thr Asp Ala Ile Arg Arg Trp Asp Leu Glu Ala Met Glu Gly
            340                 345                 350

Leu Pro Glu Tyr Met Lys Ile Cys Tyr Met Ala Leu Tyr Asn Thr Thr
        355                 360                 365

Asn Glu Val Cys Tyr Lys Val Leu Arg Asp Thr Gly Arg Ile Val Leu
    370                 375                 380

Leu Asn Leu Lys Ser Thr Trp Ile Asp Met Ile Glu Gly Phe Met Glu
385                 390                 395                 400

Glu Ala Lys Trp Phe Asn Gly Ser Ala Pro Lys Leu Glu Glu Tyr
                405                 410                 415

Ile Glu Asn Gly Val Ser Thr Ala Gly Ala Tyr Met Ala Phe Ala His
            420                 425                 430

Ile Phe Phe Leu Ile Gly Glu Gly Val Thr His Gln Asn Ser Gln Leu
        435                 440                 445

Phe Thr Gln Lys Pro Tyr Pro Lys Val Phe Ser Ala Ala Gly Arg Ile
    450                 455                 460

Leu Arg Leu Trp Asp Asp Leu Gly Thr Ala Lys Glu Glu Gln Glu Arg
465                 470                 475                 480

Gly Asp Leu Ala Ser Cys Val Gln Leu Phe Met Lys Glu Lys Ser Leu
                485                 490                 495

Thr Glu Glu Glu Ala Arg Ser Arg Ile Leu Glu Glu Ile Lys Gly Leu
            500                 505                 510

Trp Arg Asp Leu Asn Gly Glu Leu Val Tyr Asn Lys Asn Leu Pro Leu
        515                 520                 525

Ser Ile Ile Lys Val Ala Leu Asn Met Ala Arg Ala Ser Gln Val Val
    530                 535                 540

Tyr Lys His Asp Gln Asp Thr Tyr Phe Ser Ser Val Asp Asn Tyr Val
545                 550                 555                 560

Asp Ala Leu Phe Phe Thr Gln
                565

<210> SEQ ID NO 3
<211> LENGTH: 591
<212> TYPE: PRT
```

<213> ORGANISM: Salvia officinalis

<400> SEQUENCE: 3

```
Met Ser Ser Leu Ile Met Gln Val Val Ile Pro Lys Pro Ala Lys Ile
1               5                   10                  15

Phe His Asn Asn Leu Phe Ser Val Ile Ser Lys Arg His Arg Phe Ser
            20                  25                  30

Thr Thr Ile Thr Thr Arg Gly Gly Arg Trp Ala His Cys Ser Leu Gln
        35                  40                  45

Met Gly Asn Glu Ile Gln Thr Gly Arg Arg Thr Gly Gly Tyr Gln Pro
    50                  55                  60

Thr Leu Trp Asp Phe Ser Thr Ile Gln Leu Phe Asp Ser Glu Tyr Lys
65                  70                  75                  80

Glu Glu Lys His Leu Met Arg Ala Ala Gly Met Ile Ala Gln Val Asn
                85                  90                  95

Met Leu Leu Gln Glu Glu Val Asp Ser Ile Gln Arg Leu Glu Leu Ile
            100                 105                 110

Asp Asp Leu Arg Arg Leu Gly Ile Ser Cys His Phe Asp Arg Glu Ile
        115                 120                 125

Val Glu Ile Leu Asn Ser Lys Tyr Tyr Thr Asn Asn Glu Ile Asp Glu
130                 135                 140

Ser Asp Leu Tyr Ser Thr Ala Leu Arg Phe Lys Leu Leu Arg Gln Tyr
145                 150                 155                 160

Asp Phe Ser Val Ser Gln Glu Val Phe Asp Cys Phe Lys Asn Asp Lys
                165                 170                 175

Gly Thr Asp Phe Lys Pro Ser Leu Val Asp Asp Thr Arg Gly Leu Leu
            180                 185                 190

Gln Leu Tyr Glu Ala Ser Phe Leu Ser Ala Gly Glu Glu Thr Leu
        195                 200                 205

His Leu Ala Arg Asp Phe Ala Thr Lys Phe Leu His Lys Arg Val Leu
    210                 215                 220

Val Asp Lys Asp Ile Asn Leu Leu Ser Ser Ile Glu Arg Ala Leu Glu
225                 230                 235                 240

Leu Pro Thr His Trp Arg Val Gln Met Pro Asn Ala Arg Ser Phe Ile
                245                 250                 255

Asp Ala Tyr Lys Arg Arg Pro Asp Met Asn Pro Thr Val Leu Glu Leu
            260                 265                 270

Ala Lys Leu Asp Phe Asn Met Val Gln Ala Gln Phe Gln Gln Glu Leu
        275                 280                 285

Lys Glu Ala Ser Arg Trp Trp Asn Ser Thr Gly Leu Val His Glu Leu
    290                 295                 300

Pro Phe Val Arg Asp Arg Ile Val Glu Cys Tyr Tyr Trp Thr Thr Gly
305                 310                 315                 320

Val Val Glu Arg Arg Glu His Gly Tyr Glu Arg Ile Met Leu Thr Lys
                325                 330                 335

Ile Asn Ala Leu Val Thr Thr Ile Asp Asp Val Phe Asp Ile Tyr Gly
            340                 345                 350

Thr Leu Glu Glu Leu Gln Leu Phe Thr Thr Ala Ile Gln Arg Trp Asp
        355                 360                 365

Ile Glu Ser Met Lys Gln Leu Pro Pro Tyr Met Gln Ile Cys Tyr Leu
    370                 375                 380

Ala Leu Phe Asn Phe Val Asn Glu Met Ala Tyr Asp Thr Leu Arg Asp
385                 390                 395                 400

Lys Gly Phe Asn Ser Thr Pro Tyr Leu Arg Lys Ala Trp Val Asp Leu
```

```
                405                 410                 415
Val Glu Ser Tyr Leu Ile Glu Ala Lys Trp Tyr Tyr Met Gly His Lys
            420                 425                 430

Pro Ser Leu Glu Glu Tyr Met Lys Asn Ser Trp Ile Ser Ile Gly Gly
        435                 440                 445

Ile Pro Ile Leu Ser His Leu Phe Phe Arg Leu Thr Asp Ser Ile Glu
    450                 455                 460

Glu Glu Asp Ala Glu Ser Met His Lys Tyr His Asp Ile Val Arg Ala
465                 470                 475                 480

Ser Cys Thr Ile Leu Arg Leu Ala Asp Asp Met Gly Thr Ser Leu Asp
                485                 490                 495

Glu Val Glu Arg Gly Asp Val Pro Lys Ser Val Gln Cys Tyr Met Asn
            500                 505                 510

Glu Lys Asn Ala Ser Glu Glu Glu Ala Arg Glu His Val Arg Ser Leu
        515                 520                 525

Ile Asp Gln Thr Trp Lys Met Met Asn Lys Glu Met Met Thr Ser Ser
    530                 535                 540

Phe Ser Lys Tyr Phe Val Gln Val Ser Ala Asn Leu Ala Arg Met Ala
545                 550                 555                 560

Gln Trp Ile Tyr Gln His Glu Ser Asp Gly Phe Gly Met Gln His Ser
                565                 570                 575

Leu Val Asn Lys Met Leu Arg Gly Leu Leu Phe Asp Arg Tyr Glu
            580                 585                 590

<210> SEQ ID NO 4
<211> LENGTH: 599
<212> TYPE: PRT
<213> ORGANISM: Mentha spicata

<400> SEQUENCE: 4

Met Ala Leu Lys Val Leu Ser Val Ala Thr Gln Met Ala Ile Pro Ser
1               5                   10                  15

Asn Leu Thr Thr Cys Leu Gln Pro Ser His Phe Lys Ser Ser Pro Lys
            20                  25                  30

Leu Leu Ser Ser Thr Asn Ser Ser Arg Ser Arg Leu Arg Val Tyr
        35                  40                  45

Cys Ser Ser Ser Gln Leu Thr Thr Glu Arg Arg Ser Gly Asn Tyr Asn
    50                  55                  60

Pro Ser Arg Trp Asp Val Asn Phe Ile Gln Ser Leu Leu Ser Asp Tyr
65                  70                  75                  80

Lys Glu Asp Lys His Val Ile Arg Ala Ser Glu Leu Val Thr Leu Val
                85                  90                  95

Lys Met Glu Leu Glu Lys Glu Thr Asp Gln Ile Arg Gln Leu Glu Leu
            100                 105                 110

Ile Asp Asp Leu Gln Arg Met Gly Leu Ser Asp His Phe Gln Asn Glu
        115                 120                 125

Phe Lys Glu Ile Leu Ser Ser Ile Tyr Leu Asp His His Tyr Tyr Lys
    130                 135                 140

Asn Pro Phe Pro Lys Glu Arg Asp Leu Tyr Ser Thr Ser Leu Ala
145                 150                 155                 160

Phe Arg Leu Leu Arg Glu His Gly Phe Gln Val Ala Gln Glu Val Phe
                165                 170                 175

Asp Ser Phe Lys Asn Glu Glu Gly Glu Phe Lys Glu Ser Leu Ser Asp
            180                 185                 190

Asp Thr Arg Gly Leu Leu Gln Leu Tyr Glu Ala Ser Phe Leu Leu Thr
```

```
               195                 200                 205
Glu Gly Glu Thr Thr Leu Glu Ser Ala Arg Glu Phe Ala Thr Lys Phe
        210                 215                 220
Leu Glu Glu Lys Val Asn Glu Gly Val Asp Gly Asp Leu Leu Thr
225                 230                 235                 240
Arg Ile Ala Tyr Ser Leu Asp Ile Pro Leu His Trp Arg Ile Lys Arg
                245                 250                 255
Pro Asn Ala Pro Val Trp Ile Glu Trp Tyr Arg Lys Arg Pro Asp Met
            260                 265                 270
Asn Pro Val Val Leu Glu Leu Ala Ile Leu Asp Leu Asn Ile Val Gln
        275                 280                 285
Ala Gln Phe Gln Glu Glu Leu Lys Glu Ser Phe Arg Trp Trp Arg Asn
    290                 295                 300
Thr Gly Phe Val Glu Lys Leu Pro Phe Ala Arg Asp Arg Leu Val Glu
305                 310                 315                 320
Cys Tyr Phe Trp Asn Thr Gly Ile Ile Glu Pro Arg Gln His Ala Ser
                325                 330                 335
Ala Arg Ile Met Met Gly Lys Val Asn Ala Leu Ile Thr Val Ile Asp
            340                 345                 350
Asp Ile Tyr Asp Val Tyr Gly Thr Leu Glu Glu Leu Glu Gln Phe Thr
        355                 360                 365
Asp Leu Ile Arg Arg Trp Asp Ile Asn Ser Ile Asp Gln Leu Pro Asp
    370                 375                 380
Tyr Met Gln Leu Cys Phe Leu Ala Leu Asn Asn Phe Val Asp Asp Thr
385                 390                 395                 400
Ser Tyr Asp Val Met Lys Glu Lys Gly Val Asn Val Ile Pro Tyr Leu
                405                 410                 415
Arg Gln Ser Trp Val Asp Leu Ala Asp Lys Tyr Met Val Glu Ala Arg
            420                 425                 430
Trp Phe Tyr Gly Gly His Lys Pro Ser Leu Glu Glu Tyr Leu Glu Asn
        435                 440                 445
Ser Trp Gln Ser Ile Ser Gly Pro Cys Met Leu Thr His Ile Phe Phe
    450                 455                 460
Arg Val Thr Asp Ser Phe Thr Lys Glu Thr Val Asp Ser Leu Tyr Lys
465                 470                 475                 480
Tyr His Asp Leu Val Arg Trp Ser Ser Phe Val Leu Arg Leu Ala Asp
                485                 490                 495
Asp Leu Gly Thr Ser Val Glu Glu Val Ser Arg Gly Asp Val Pro Lys
            500                 505                 510
Ser Leu Gln Cys Tyr Met Ser Asp Tyr Asn Ala Ser Glu Ala Glu Ala
        515                 520                 525
Arg Lys His Val Lys Trp Leu Ile Ala Glu Val Trp Lys Lys Met Asn
    530                 535                 540
Ala Glu Arg Val Ser Lys Asp Ser Pro Phe Gly Lys Asp Phe Ile Gly
545                 550                 555                 560
Cys Ala Val Asp Leu Gly Arg Met Ala Gln Leu Met Tyr His Asn Gly
                565                 570                 575
Asp Gly His Gly Thr Gln His Pro Ile Ile His Gln Gln Met Thr Arg
            580                 585                 590
Thr Leu Phe Glu Pro Phe Ala
        595
```